(12) United States Patent
Andreakos et al.

(10) Patent No.: US 12,121,564 B2
(45) Date of Patent: Oct. 22, 2024

(54) USE OF LAMBDA INTERFERONS IN THE TREATMENT OF OBESITY-RELATED DISORDERS AND RELATED DISEASES

(71) Applicants: BIOMEDICAL RESEARCH FOUNDATION OF THE ACADEMY OF ATHENS, Athens (GR); Evangelos Andreakos, Athens (GR); Maria Salagianni, Athens (GR)

(72) Inventors: Evangelos Andreakos, Athens (GR); Maria Salagianni, Athens (GR)

(73) Assignees: BIOMEDICAL RESEARCH FOUNDATION OF THE ACADEMY OF ATHENS, Athens (GR); Evangelos Andreakos, Athens (GR); Maria Salagianni, Athens (GR)

( * ) Notice: Subject to any disclaimer, the term of this patent is extended or adjusted under 35 U.S.C. 154(b) by 639 days.

(21) Appl. No.: 16/604,378

(22) PCT Filed: Mar. 16, 2018

(86) PCT No.: PCT/EP2018/056712
§ 371 (c)(1),
(2) Date: Oct. 10, 2019

(87) PCT Pub. No.: WO2018/167287
PCT Pub. Date: Sep. 20, 2018

(65) Prior Publication Data
US 2020/0157167 A1    May 21, 2020

(30) Foreign Application Priority Data
Mar. 16, 2017   (EP) ..................................... 17161461

(51) Int. Cl.
| | | |
|---|---|---|
| *A61K 38/21* | (2006.01) | |
| *A61P 3/04* | (2006.01) | |
| *A61P 3/06* | (2006.01) | |
| *A61P 3/10* | (2006.01) | |
| *A61P 7/02* | (2006.01) | |
| *A61P 9/10* | (2006.01) | |
| A61K 38/00 | (2006.01) | |
| C07K 14/555 | (2006.01) | |
| C07K 14/57 | (2006.01) | |

(52) U.S. Cl.
CPC ................ *A61K 38/21* (2013.01); *A61P 3/04* (2018.01); *A61P 3/06* (2018.01); *A61P 3/10* (2018.01); *A61P 7/02* (2018.01); *A61P 9/10* (2018.01); *A61K 38/00* (2013.01); *C07K 14/555* (2013.01); *C07K 14/57* (2013.01)

(58) Field of Classification Search
CPC ......... A61K 38/21; C07K 14/555; A61P 3/04; A61P 3/06; A61P 3/10; A61P 7/02; A61P 9/10
See application file for complete search history.

(56) References Cited

U.S. PATENT DOCUMENTS

2007/0041936 A1* 2/2007 Brady ................. A61P 1/16
                                                              536/23.53
2015/0307590 A1* 10/2015 Egli ...................... C07K 14/57
                                                              424/139.1

FOREIGN PATENT DOCUMENTS

| EP | 3558342 A1 | 10/2019 |
|---|---|---|
| WO | 2009/152152 A1 | 12/2009 |
| WO | 2018115199 A1 | 6/2018 |

OTHER PUBLICATIONS

Kolchanov, 1988, Journal of Molecular Evolution, vol. 27, pp. 154-162. (Year: 1988).*
Pasquo, 2012, PLoS One, vol. 7, Issue 2, e32555 (Year: 2012).*
Donnelley et al. (2010, J of Interferon & Cytokine Research, vol. 30, No. 8, pp. 555-564) (Year: 2010).*
Kontsek et al, 2003. Acta virologica. 47: 201-215 (Year: 2003).*
Record for NCBI Protein Reference Sequence NP_742152.1, interferon lambda-1 precursor [*Homo sapiens*], record dated Mar. 15, 2023; printed from https://www.ncbi.nlm.nih.gov/protein/np_742152; 3 pages as printed; no author indicated (Year: 2023).*
Todt et al (2016. Antimicrobial Agents and Chemotherapy. 60(4): 2132-2139) (Year: 2016).*
Andersen et al, 2013 (Journal of Clinical and Translational Hepatology. 1: 116-214). (Year: 2013).*
K. Lind et al., "Induction of an Antiviral State and Attenuated Coxsackievirus Replication in Type III Interferon-Treated Primary Human Pancreatic Islets", Journal of Virology, vol. 87, No. 13, May 1, 2013, pp. 7646-7654.
Peter M. George et al., "Pharmacology and therapeutic potential of interferons", Pharmacology & Therapeutics, vol. 135, No. 1, Mar. 27, 2012, pp. 44-53.
Akrivi Chrysanthopoulou et al., "Interferon lambsa1/IL-29 and inorganic polyphosphate are novel regulators of neutrophil-driven thromboinflammation: IFN-[lambda] and PolyP in neutrophil thromboinflamation", The Journal of Pathology, Jul. 5, 2017, 36 pages.
Alain Camilleri, International Search Report and Written Opinion of the International Searching Authority dated Jun. 4, 2018, PCT Application No. PCT/EP2018/056712, 13 pages.
Office Action for the corresponding European Application No. 17 161 461.3 dated Apr. 20, 2023, 5 pages.

\* cited by examiner

*Primary Examiner* — Zachary C Howard
(74) *Attorney, Agent, or Firm* — MH2 TECHNOLOGY LAW GROUP, LLP

(57) ABSTRACT

The invention relates to the field of treatment or prevention of obesity-related disorders, atherosclerosis or a coagulation disorder. In particular, the present invention relates to the use of an activator of IFNλ receptor for the treatment or prevention of such disorders or conditions, and corresponding methods of treatment.

21 Claims, 16 Drawing Sheets
Specification includes a Sequence Listing.

USE OF LAMBDA INTERFERONS IN THE TREATMENT OF OBESITY-RELATED DISORDERS AND RELATED DISEASES

CROSS-REFERENCE TO RELATED APPLICATIONS

This application is a U.S. National Stage application of PCT/EP2018/056712 filed 16 Mar. 2018, which claims priority to European Patent Application No. EP17161461.3 filed 16 Mar. 2017, the entire disclosures of which are herein incorporated by reference.

The instant application contains a Sequence Listing which has been submitted electronically in ASCII format and is hereby incorporated by reference in its entirety. Said ASCII copy, created on 26 Sep. 2023, is named PCT_sequence-listing_as filed DFMP 126 US. SL .txt and is 9 Kilobytes in size.

FIELD OF THE INVENTION

The present invention relates to the field of treatment or prevention of obesity-related disorders, such as obesity, prediabetes, diabetes, insulin resistance, metabolic disease, metabolic syndrome, atherosclerosis, coagulation, hyperlipidemia and dyslipidemia, cardiovascular diseases and pathological conditions associated therewith. In particular, the present invention relates to the use of an activator of IFNλ receptor for the treatment or prevention of such disorders or conditions, and corresponding methods of treatment.

BACKGROUND

Molecular Biology of IFNλs

Lambda IFNs (IFNλs), type III IFNs or IL-28/29 constitute one of the most recent additions to the interferon family (Lazear et al., 2015). They consist of four members in humans (IFNλ1/IL-29, IFNλ2/IL-28A, IFNλ3/IL-28B and IFNλ4) and two in mice (IFNλ2/IL-28A, IFNλ3/IL-28B) (Kotenko et al., 2003; Sheppard et al., 2003; Prokunina-Olsson et al., 2013; Galani et al. 2015). In humans, all of the corresponding genes are closely positioned on chromosome 19. In mice, a similar genomic organization is found on chromosome 5, although in this case IFNλ1 is a pseudogene; there is a stop codon in the first exon that prevents the full length transcript from been expressed (Lasfar et al., 2006).

As their name implies, IFNλs (type III IFNs) share homology with type I and type II IFNs. However, they also share homology with the IL-10 superfamily and are structurally more similar to IL-10 family members than type I IFNs (Gad et al., 2009). In all cases, this homology is low: 15-19% in amino acid sequence identity with IFNα and IL-22, and 11-13% in amino acid sequence identity with IL-10 (Sheppard et al., 2003). Among the IFNλ family, IFNλ2 and IFNλ3 are more closely related to one another than either of them is to IFNλ1: IFNλ1 and IFNλ2 share 81% amino acid sequence identity, while IFNλ2 and IFNλ3 are almost identical, with 96% amino acid sequence identity (Sheppard et al., 2003). This is because IFNλ2 and IFNλ3 are the result of a recent duplication event during evolution. It is noteworthy that, in contrast to type I IFNs that completely lack introns, IFN-λ genes have an organization similar to the IL-10 gene family, with multiple exons and introns (Sheppard et al., 2003).

IFNλs signal through a distinct heterodimeric receptor complex consisting of the unique IFNλRα (IL28Rα/IL28Rα/CRF2-12) chain, which provides high affinity for the ligand and confers ligand specificity, and the IL-10Rβ/CRF2-4 chain, which is common to all IL-10 superfamily members (IL-10, IL-19, IL-20, IL-22, IL-24 and IL-26) and has a relatively long intracellular domain comprising a docking site for downstream signaling (Kotenko et al., 2003, Sheppard et al., 2003). The IFNλ receptor complex forms sequentially in a two-step binding event. First, the IFNλRα subunit binds to IFNλ with high affinity, which in the second step assemble to the IL-10Rβ subunit, forming the ternary complex at a 1:1:1 IFNλ/IFNλRα/IL-10Rβ stochiometry (Mendoza et al., 2017). Yet, IFNλs induce downstream signaling that bears notable resemblance to that of type I IFNs; it involves the phosphorylation of JAK-family kinases, and the activation of STAT and interferon-regulated (transcription) factors (IRFs), driving the expression of interferon-stimulated genes (ISGs) and the induction of antiviral responses (Durbin et al., 2013; Kotenko, 2011).

IFNλs are induced in response to viral infection. Numerous viruses have now been shown to trigger IFNλ production in many cell types including influenza, rhinovirus, Sendai Virus, Hepatitis C virus, hepatotropic viruses, vesicular stomatitis virus (VSV), lymphocytic choriomeningitis virus (LCMV), VSV or HSV-2, Reovirus (Reo), Sindbis virus (SV), Dengue virus 2 (DV) and encephalomyocarditis virus (Ank et al., 2006, Kotenko et al., 2003, Sheppard et al., 2003). Diverse bacterial pathogens such as *Listeria monocytogenes, Staphylococcus aureus, Staphylococcus epidermidis* and *Enterococcus faecalis* also induce IFNλs. In line with that, TLR and RIG-I ligands constitute potent inducers of IFNλs in vitro and in vivo.

Although a broad range of pathogens are capable of inducing IFNλs, the cellular sources of IFNλs are relatively limited and include epithelial cells, especially at mucosal interfaces, conventional and plasmacytoid dendritic cells, and monocytes. IFNλs are regulated at the level of transcription and depend on intracellular sensors of viral infection and downstream molecules such as TLR3, retinoic acid-inducible gene I (RIG-I), interferon-β promoter stimulator 1 (IPS-1), TANK-binding kinase 1 (TBK1), and IRFs, which also control type I IFN production (Onoguchi et al., 2007). Accordingly, several IRF and NF-κB binding sites have been identified in the promoter regions of the human IFNλ genes which may be used differentially to drive their expression in different cells and in response to different stimuli (Onoguchi et al., 2007, Osterlund et al., 2007). Thus, IFNλ1 is mostly regulated by virus-activated IRF3 and IRF7, similar to the IFNβ gene, whereas IFNλ2/3 gene expression is mainly controlled by IRF7, resembling the induction of IFNα genes (Osterlund et al., 2007). In hepatocytes, IRF1 may be equally important for IFNλ1 mRNA induction (Odendall et al., 2014). NF-κB is also involved in the induction of IFNλs. A cluster of NF-κB-binding sites distal to the IFNλ1 promoter has been found that are required for maximal IFNλ1 production in human monocyte-derived DCs following LPS stimulation (Thomson et al., 2009). Nevertheless, although disruption of both IRF and NF-κB sites significantly reduces transcription of IFNλs, residual activation can still be detected, suggesting yet unidentified cis-regulatory elements that guide IFNλ expression (Onoguchi et al., 2007). Furthermore, the organization of IFNλ genes with multiple exons and introns suggests additional post-transcriptional regulation, absent from type I IFN genes, which may be crucial for IFNλ production.

The fact that IFNλs share homology, expression patterns, signaling cascades and antiviral functions with type I IFNs fueled initial speculation that IFNλs are functionally redundant to type I IFNs. However, it was later shown that IFNλs and IFNλR1 exhibit a much more restricted pattern of expression compared to type I IFNs and the type I IFN receptor (IFNAR1/IFNAR2) which is present ubiquitously in all nucleated cells. IFNλR1 is mostly expressed in cells of epithelial origin including respiratory or intestinal epithelial cells, hepatocytes and keratinocytes (Sommereyns et al., 2008), although cells of the myeloid lineage such as cDCs (Mennechet and Uze, 2006) and pDCs also express the receptor. This suggested that IFNλs may be particularly important at mucosal interfaces and the liver, with their 'rate-limiting' role being governed by ligand availability and receptor distribution (Durbin et al., 2013). In support of that, compartmentalization of the two IFN systems in the gastrointestinal tract (Hernandez et al., 2015; Mahlakoiv et al., 2015; Pott et al., 2011) and the liver has been demonstrated.

In the respiratory tract, such clear-cut distinction between receptor-ligand availability in epithelial and immune cells has not been described but IFNλs are broadly considered as important players of antiviral defence there as well (Mordstein et al., 2010a). They are induced first in response to infection and mediate front line antiviral protection without inducing inflammation and compromising host fitness (Galani et al., 2017). This is in contrast to type I IFNs which are induced later and act by enhancing pro-inflammatory responses as well.

Therapeutic Applications of IFNλs

Viral Infections

By virtue of their resemblance to type I IFNs, IFNλs have attracted great interest in the treatment of viral infections. IFNλs were shown to inhibit hepatitis B and C replication in vitro in hepatocyte cell lines. Inhibition was equally efficient as that of type I IFNs (Robek et al., 2005), which are currently used in combination with the antiviral compound ribavirin as the standard method of care for hepatitis C patients. However, as type I IFNs are toxic leading to several adverse effects including flu-like disease and neurological as well as neuropsychiatric manifestations (Aspinall and Pockros, 2004), IFNλs have attracted attention as a safer alternative. Thus, a pegylated form of IFNλ1 (ZymoGenetics Inc./Bristol Myers Squibb) reached phase 3 trials for the treatment of hepatitis C infection. Data reported showed a positive outcome of the therapy which is advantageous over IFN-α treatments, with fewer side effects and good clinical response. This is likely to be due to the more restricted pattern of expression of the IFNλR, which is absent from hematopoietic progenitor cells and the CNS, and thus does not provoke cytopenia, or neurological disorders commonly seen following IFN-α treatment (Ramos, 2010; Sommereyns et al., 2008).

In the respiratory system, deficient IFNλ production has been linked to asthma severity and disease exacerbations due to higher viral load and airway inflammation (Bullens et al., 2008, Contoli et al., 2006, Koltsida et al., 2011). In experimental models of asthma, IFNλ administration has been further shown to suppress respiratory viral infections and inhibit allergic airway inflammation and disease. This provides a strong rationale for the therapeutic administration of recombinant IFNλs in asthma exacerbations with the aim to reduce viral load while at the same time inhibiting the underlying immunological basis of the disease. Clinical trials in that respect are therefore eagerly awaited.

Finally, IFNλs are promising therapeutics for the treatment of diverse viral infections and cancer. For example, as keratinocytes and melanocytes express IFNλR and respond to IFNλs (Witte et al., 2009), several skin viral infections and carcinomas may be treatable through the application of these cytokines. In addition, several gastrointestinal and systemic infections may also be tackled through the administration of IFNλs. It is noteworthy that IFNλs may also instruct adaptive immunity and potentiate CD8+ T cell cytotoxic functions in vivo in mice (Misumi and Whitmire, 2014) and macaques (Morrow et al., 2010). They are therefore attractive candidates for boosting anti-microbial immune defenses and enhancing the efficacy of vaccines.

Immunomodulation

In addition to inhibiting viral replication, type III IFNs may also influence the innate and adaptive immune response. Initial experiments with IFNλs showed that these cytokines can up-regulate MHC class I expression comparable to type I IFNs (Kotenko et al., 2003). High expression of MHC class I and II molecules on antigen presenting cells, tumor cells or infected epithelial cells is generally associated with induction of more effective host immunity. Subsequent studies suggested that IFNλ1 can up-regulate IL-6, -8 and -10 cytokine production in human monocytes (Jordan et al., 2007a) and induce MIG/CXCL9, IP-10/CXCL10 and I-TAC/CXCL11, chemokines typically triggered by IFNγ (Pekarek et al., 2007). The caveat in these studies, however, has been that they were all performed in mixed human peripheral blood mononuclear cell cultures, leaving open the possibility that many of these effects are indirect. Several reports have also proposed a role of IFNλs in the regulation of DC function. Megjugorac et al. and Yin et al. indicated that human pDCs produce IFNλs and respond to them by upregulating CD80 and ICOS-L expression (Megjugorac et al., 2009, Yin et al., 2012). Mennechet et al. showed that IFN-λ treatment of human conventional DCs (cDCs) induced the proliferation of Foxp3+ suppressor T cells, and proposed an immunoregulatory function of type III IFNs (Mennechet and Uze, 2006). Finally, Koltsida et al. demonstrated that IFNλs signal on cDCs to down-regulate OX40L, up-regulate IL-12 and mediate Th1 polarization in the context of respiratory inflammation (Koltsida et al., 2011). Other studies in vitro, have also suggested a role of IFNλs in the modulation of the Th1/Th2 response through the reduction of GATA3 and IL-13, and possibly the increase of IFN-γ (Jordan et al., 2007b) (Dai et al., 2009). However, whether IFNλs can directly act on human CD4+ T cells, or whether this is mediated through professional antigen-presenting cells such as DCs has remained controversial.

Asthma, Allergic & Respiratory Diseases

In addition to anti-viral immunity, two important studies hinted to a role of IFNλs in allergic airway disease (Contoli et al., 2006, Bullens et al., 2008). Contoli et al. reported an impaired production of IFNλs by primary bronchial epithelial cells and alveolar macrophages during allergic asthma exacerbations in patients upon RV infections. IFNλ levels were inversely correlated to viral load and disease severity (Contoli et al., 2006). Bullens et al. detected increased levels of IFNλ mRNA in the sputum of asthmatics versus healthy individuals, in the absence of evidence of viral infection, and these correlated to milder asthma symptoms in steroid-naïve patients (Bullens et al., 2008). Yet, an immunoprotective role of IFNλs in asthma was demonstrated later on by a third study that provided in vivo evidence that IFNλs could up-regulate IL-12, induce Th1 immunity and suppress pathogenic Th2 mediated immune responses that drive asthma (Koltsida et al., 2011). These concerted antiviral and anti-inflammatory actions of IFNλs in the lung establish them as attractive potential immunotherapeutic compounds for the treatment of asthma exacerbations usually triggered by viruses and mediated by augmented Th2 responses.

Cancer, Anti-Tumour and Other Functions of IFNλs

Type III IFNs were also shown to exhibit anti-tumor activity. In vitro, IFNλs exerted anti-proliferative effects in the pancreatic neuroendocrine cell line BON-1 (Zitzmann et al., 2006) and the human keratinocyte cell line HaCaT (Maher et al., 2008), and induced apoptosis in HT29 colorectal adenocarcinoma cells (Li et al., 2008). B16 melanoma cells engineered to constitutively express mouse IFNλ2, were less tumorigenic in mice in vivo, an effect that was mediated via the action of IFNλ2 on host immune cells, rather than directly on tumor cells (Lasfar et al., 2006). Similarly, Numasaki et al. documented reduced tumor growth and fibrosarcoma metastases in the lungs of mice treated with IFNλ, in a process that involved the action of immune cells (Numasaki et al., 2007). In a mouse model of hepatocellular carcinoma, IFNλ acted on DCs to potentiate the anti-tumor action of NK cells (Abushahba et al., 2010). To the contrary, Sato et al showed that the anti-tumor effect of IFNλs in murine models of B16 melanoma and Colon26 cancer cells was exerted by IFNλ through both direct and indirect effects; inhibition of tumor growth and induction of NK/NKT cell cytotoxic activity in vivo (Sato et al., 2006).

Obesity-Related Disorders and their Treatment

Disorders such as obesity, prediabetes, diabetes, insulin resistance, metabolic syndrome, atherosclerosis, cardiovascular diseases, hyperlipidemia or dyslipidemia and the pathologies related thereto represent major challenges to public health and the healthcare systems in terms of morbidity, mortality and costs. They are highly prevalent diseases that can also lead to myocardial infarction, heart disease and stroke, or even increase the risk for various forms of cancer.

Obesity, in particular, is formally recognized as a global epidemic of our times, with an estimated worldwide prevalence of 1.9 billion overweight (30% of the global population) and 600 million obese adults (World Health Organization 2014). Despite major efforts of academic research and the pharmaceutical industry to understand the cause(s) of this disease and to develop effective medications to prevent or treat obesity and related diseases, medical treatments remain limited and in many cases non-existent.

Thus, despite existing preventative or therapeutic approaches there remains a need for effective approaches to the treatment or prevention of obesity-related disorders such as those listed above.

SUMMARY OF THE INVENTION

The present invention is based on the surprising finding that an activator of IFNλ receptor is effective in preventing or treating obesity-related disorders, atherosclerosis and coagulation disorders.

The inventors found that administration of an activator of IFNλ receptor reduces proinsulin C-peptide, insulin and leptin levels in an in vivo animal model. Administration of an activator of IFNλ receptor further results in weight loss by lowering food intake and prioritizing fat over carbohydrate consumption. Conversely, the inventors could demonstrate that lack of a functional IFNλRα, and thus inability of any activator of IFNλ receptor to act, induces weight gain. Also, the inventors could show that administration of an activator of IFNλ receptor enhances insulin sensitivity and treats insulin resistance in mice. They could also establish a causal role of dysfunctional IFNλRα in insulin resistance. Additionally, treatment with an activator of IFNλ receptor decreases atherosclerosis and risk of thromboembolytic complications by reducing atherosclerotic lesion size and intralesional inflammation as indicated by macrophage accumulation in the plaques. The inventors could also show that IFNλ reduces pro-coagulant and pro-thrombotic activities.

Accordingly, the present invention provides an activator of IFNλ receptor for use in the prevention or treatment of obesity-related disorders, atherosclerosis or coagulation disorders. Further, a method of preventing or treating obesity-related disorders, atherosclerosis or coagulation disorders comprising administering a therapeutically effective amount of an activator of IFNλ receptor to a subject in need of such treatment or prevention is provided.

Further provided is a method of determining susceptibility of a subject suffering from an obesity-related disorder, atherosclerosis or a coagulation disorder to treatment with an activator of IFNλ receptor, wherein the method comprises administering the activator of IFNλ receptor to the subject and determining the effect on the obesity-related disorder, atherosclerosis or the coagulation disorder. Also provided is an activator of IFNλ receptor for use in determining susceptibility of a subject suffering from an obesity-related disorder, atherosclerosis or a coagulation disorder to treatment with the activator of IFNλ receptor, wherein the activator of IFNλ receptor is administered to the subject and the effect on the obesity-related disorder, atherosclerosis or the coagulation disorder is determined.

In one embodiment, the present invention relates to an activator of IFNλ receptor for use in the therapeutic reduction of body weight in a subject. The invention also provides a therapeutic method for reducing body weight in a subject comprising administering an activator of IFNλ receptor to the subject.

In one embodiment, the present invention relates to the use of an activator of IFNλ receptor for the non-therapeutic reduction of body weight. The invention also provides a method for reducing body weight in a subject comprising administering an activator of IFNλ receptor to the subject.

Also provided is a pharmaceutical composition comprising an activator of IFNλ receptor and a pharmaceutically acceptable excipient for use in the treatment of obesity-related disorders, atherosclerosis and coagulation disorders.

In a preferred embodiment, the activator of IFN receptor is IFNλ. In a particularly preferred embodiment, the IFNλ is human IFNλ. Furthermore, the IFNλ, and in particular the human IFNλ, may be selected from the group consisting of IFNλ1, IFNλ2, IFNλ3 and IFNλ4.

Highly purified neutrophils from wild type C57BL/6 mice were exposed to 100 ng/ml of recombinant IFNλ3 for 8 h and transcriptional analysis was performed by RNA sequencing. Relative expression levels of tissue factor (TF), Cathepsin G (CTSG), elastase (ELANE), peptidyl arginine deiminase type IV (PADI4) and IL-1ra are shown. Data are expressed as mean±SEM of n=3 independent experiments. *p<0.05, **p<0.01

Figure 10:
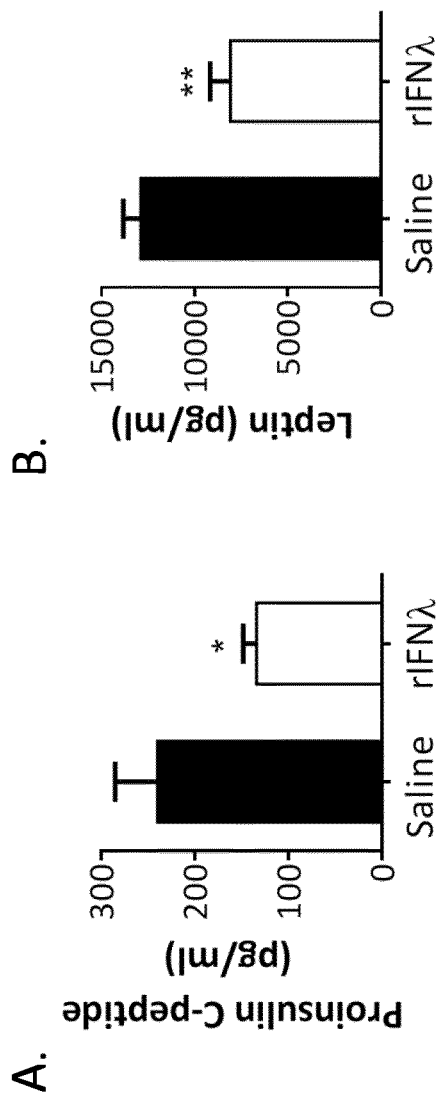

FIG. 10. Prophylactic Administration of Recombinant IFNλ Lowers Proinsulin C-Peptide and Leptin Levels in the Serum of C57BL/6 Mice 6-week old wild type C57BL/6 mice fed with high fat diet (HFD) from week 6 onwards were treated with recombinant IFNλ3 (5 μg/mouse) twice per week for a total of 12 weeks. Control mice received saline. Sera were collected at week 18 and analyzed for the presence of proinsulin C-peptide (A) and leptin (B). Data are expressed as mean±SEM of n=7-8 mice per group. *p<0.05 **p<0.01, FIG. 11. Prophylactic Administration of Recombinant IFNλ Lowers TNF and MCP-1 Levels in the Serum of C57BL/6 Mice 6-week old wild type C57BL/6 mice fed with high fat diet (HFD) from week 6 onwards were treated with recombinant IFNλ3 (5 μg/mouse) twice per week for a total of 12 weeks. Control mice received saline. Sera were collected at week 18 and analyzed for the presence of TNF (A) and MCP-1 (B). Data are expressed as mean±SEM of n=7-8 mice per group. *p<0.05 p<0.01, FIG. 12. Prophylactic Administration of Recombinant IFNλ Prevents the Development of Diet-Induced Obesity in C57BL/6 Mice 6-week old wild type C57BL/6 mice fed with high fat diet (HFD) from week 6 onwards were treated with recombinant IFNλ3 (5 μg/mouse) twice per week for a total of 12 weeks. Control mice received saline. Weight was measured weekly from week 6 until week 18. Data are expressed as mean±SEM of n=7-8 mice per group. *p<0.001

Figure 13:
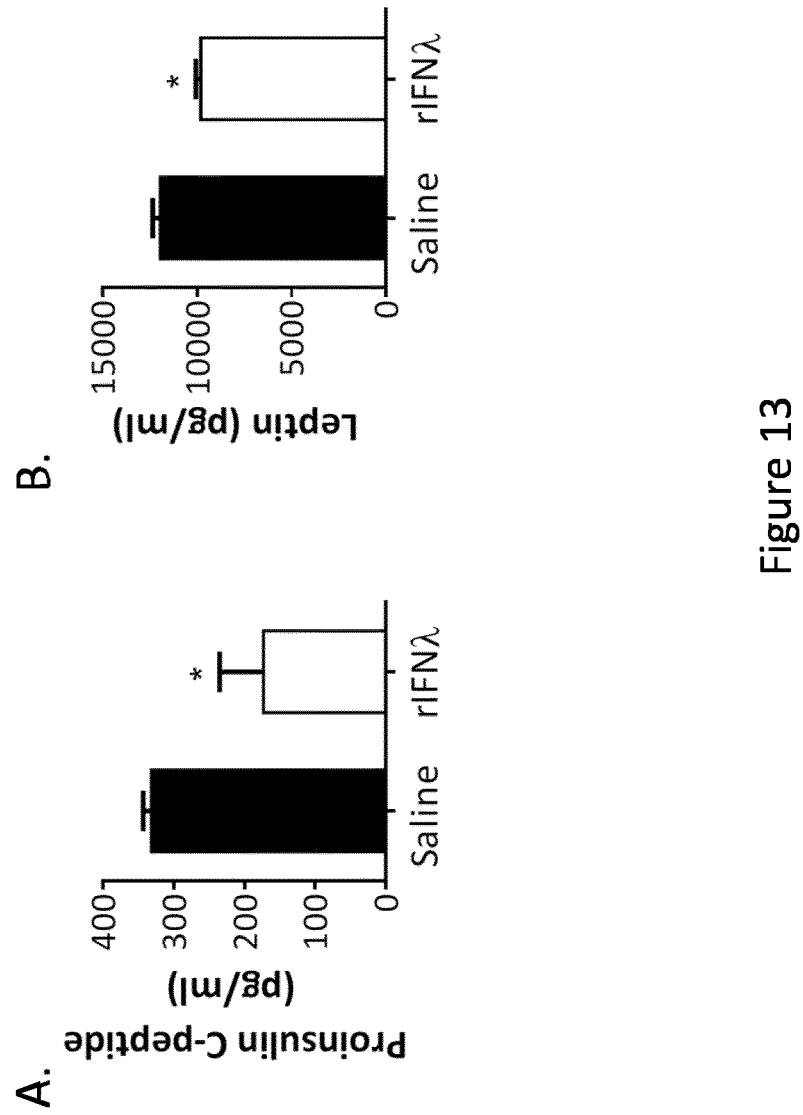

FIG. 13. Therapeutic Administration of Recombinant IFNλ Lowers Proinsulin C-Peptide and Leptin Levels in the Serum 10-week old wild type C57BL/6 mice fed with high fat diet (HFD) from week 6 onwards were treated therapeutically with recombinant IFNλ3 (5 μg/mouse, arrow) twice per week for a total of 8 weeks. Control mice received saline. Sera were collected at week 18 and analyzed for the presence of proinsulin C-peptide (A) and leptin (B). Data are expressed as mean±SEM of n=4 mice per group.*p<0.05

Figure 14:
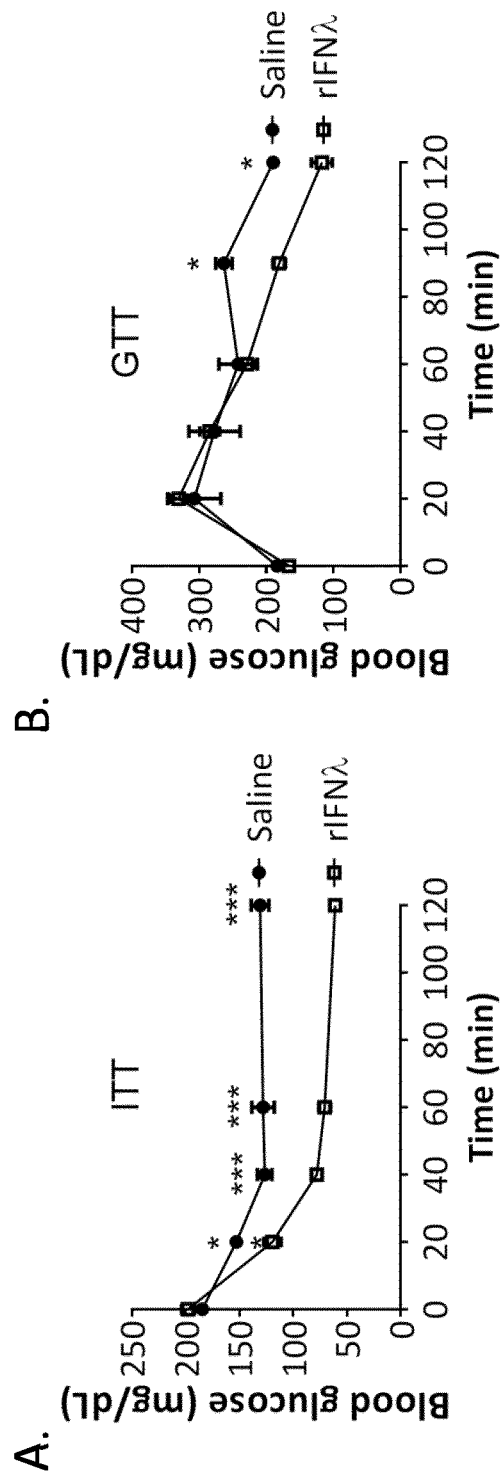

FIG. 14. Recombinant IFNλ Restores Insulin Sensitivity in C57BL/6 Mice 10-week old wild type C57BL/6 mice fed with high fat diet (HFD) from week 6 onwards were treated therapeutically with recombinant IFNλ3 (5 μg/mouse, arrow) twice per week for a total of 8 weeks. Control mice received saline. GTT was performed following an overnight fast. Mice received an intraperitoneal injection of 10% D-glucose (1 g/kg body weight) for GTT and an intraperitoneal injection of human regular insulin at a dose of 0.75 U/kg body weight for ITT. Tail vein blood (5-10 al) for OTT was assayed for glucose at 0, 20, 40, 60, 90 and 120 minutes (B)

and for ITT at 0, 20, 40, 60 and 120 minutes (A) with Bayer's Contour Next Meter. Data are expressed as mean ±SEM of n=3-5 mice per group. #p<0.05, *** p<0.001

Figure 15:
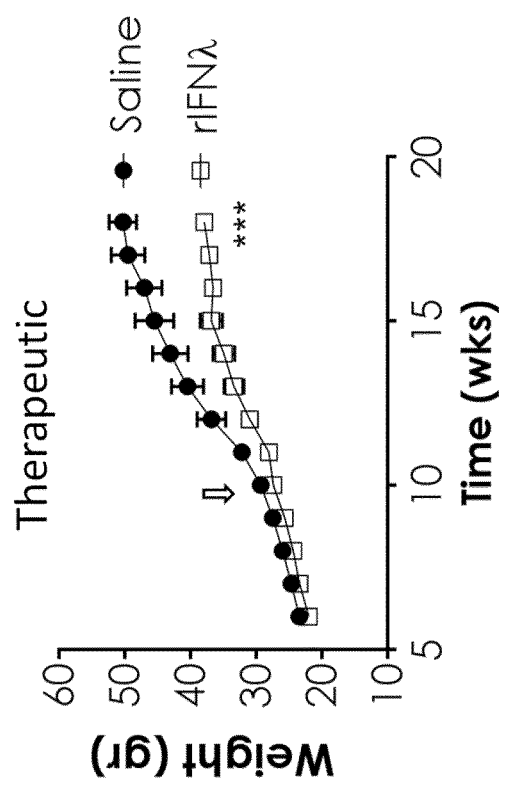

FIG. 15. Therapeutic Administration of Recombinant IFNλ Treats Diet-Induced Obesity in C57BL/6 Mice 10-week old wild type C57BL/6 mice fed with high fat diet (HFD) from week 6 onwards were treated therapeutically with recombinant IFNλ3 (5 µg/mouse, arrow) twice per week for a total of 8 weeks. Control mice received saline. Weight was measured weakly from week 6 until week 18. Data are expressed as mean±SEM of n=4 mice per group. ***p<0.001

Figure 16:
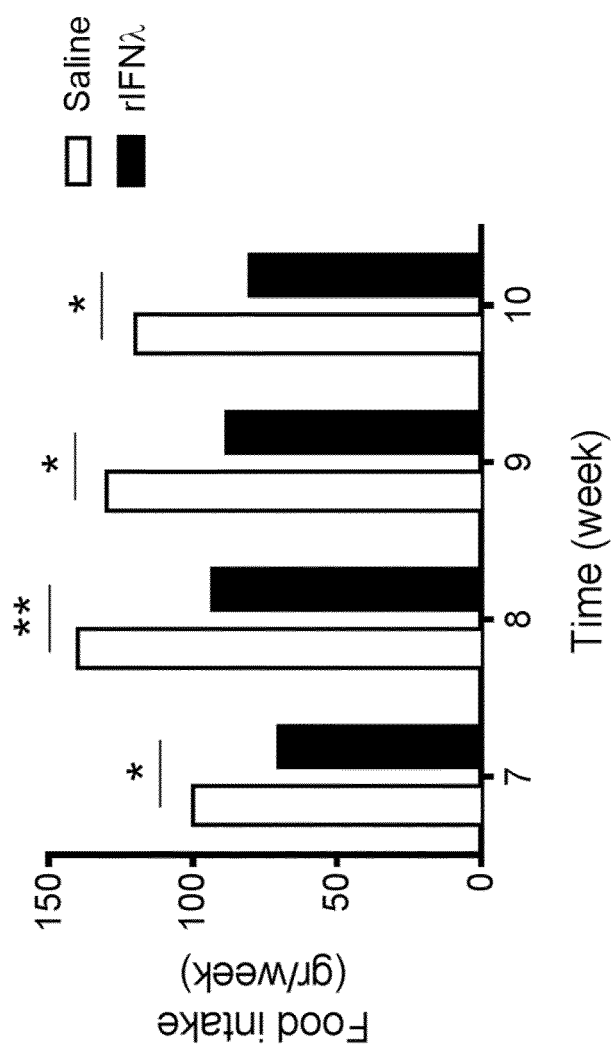

FIG. 16. Recombinant IFNλ Administration Lowers Food Consumption in C57BL/6 Mice 6-week old wild type C57BL/6 mice fed with high fat diet (HFD) from week 6 onwards were treated with recombinant IFNλ3 (5 µg/mouse) twice per week for a total of 4 weeks. Control mice received saline. Food consumption in gr/week was measured weakly from week 7 until week 10. Data are expressed as mean±SEM of n=4 mice per group. *p<0.05, **p<0.01

Figure 17:
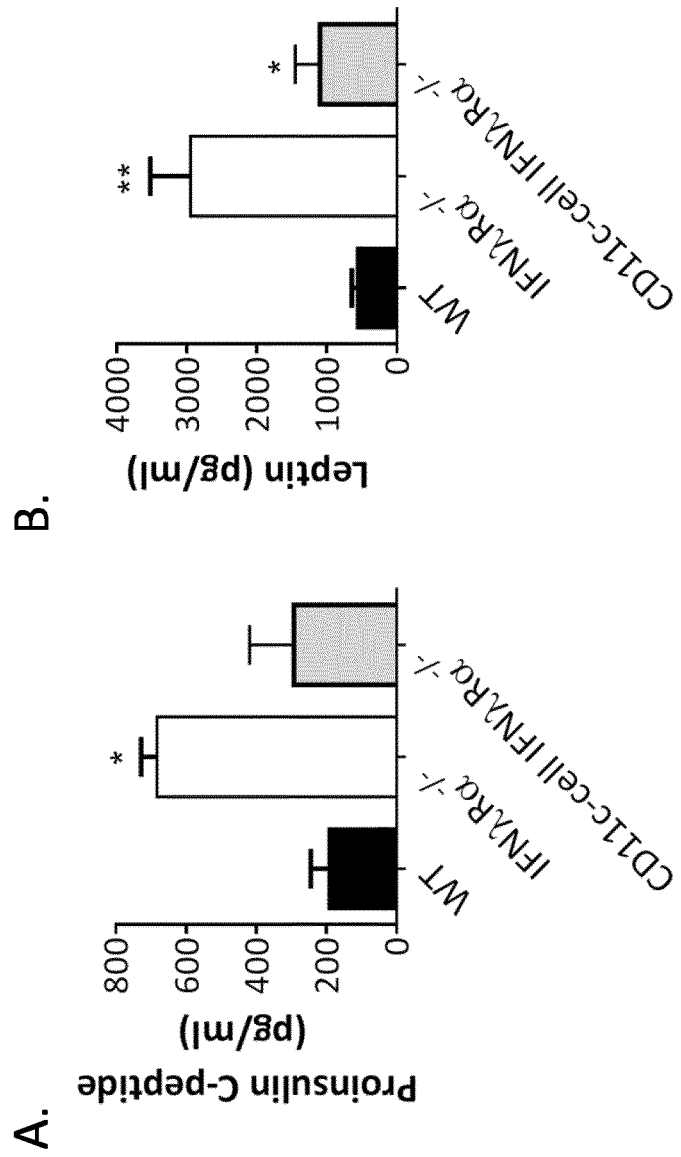

FIG. 17. IFNλRα$^{-/-}$ Mice Fed a Normal Chow Diet Exhibit Higher Proinsulin C-Peptide and Leptin Levels in the Serum Wild type (WT) C57BL/6 mice, global IFNλRα$^{-/-}$ mice and CD11c$^{+}$ cell-specific IFNλRα$^{-/-}$ mice were fed a normal chow diet (NCD). Sera were collected at week 10 and analyzed for the presence of proinsulin C-peptide (A) and leptin (B). Data are expressed as mean±SEM of n=4 mice per group.*p<0.05, **p<0.01

Figure 18:
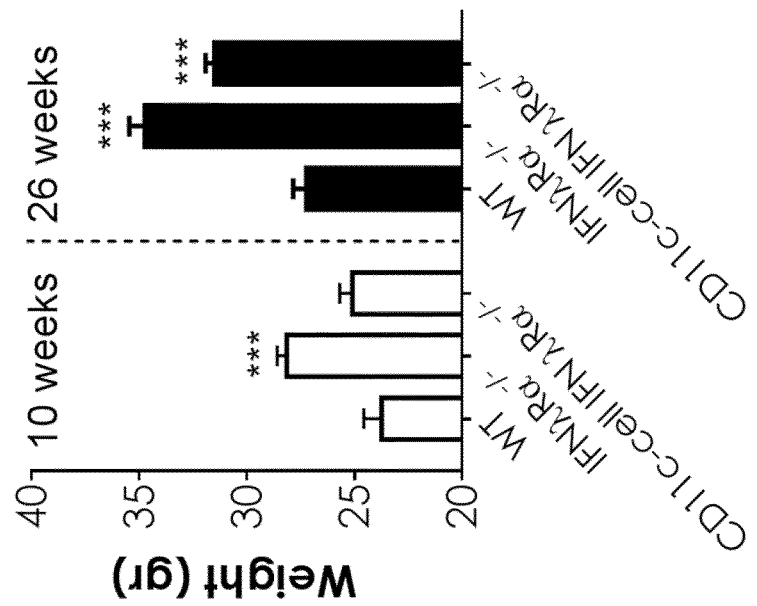

FIG. 18. IFNλRα$^{-/-}$ Mice Fed a Normal Chow Diet Develop Obesity

Wild type (WT) C57BL/6 mice, global IFNλRα$^{-/-}$ mice and CD11c$^{-}$ cell-specific IFNλRα$^{-/-}$ mice were fed a normal chow diet (NCD) and their weight measured at week 10 and week 26. Data are expressed as mean±SEM of n=10-12 mice per group. ***p<0.001

Figure 19:
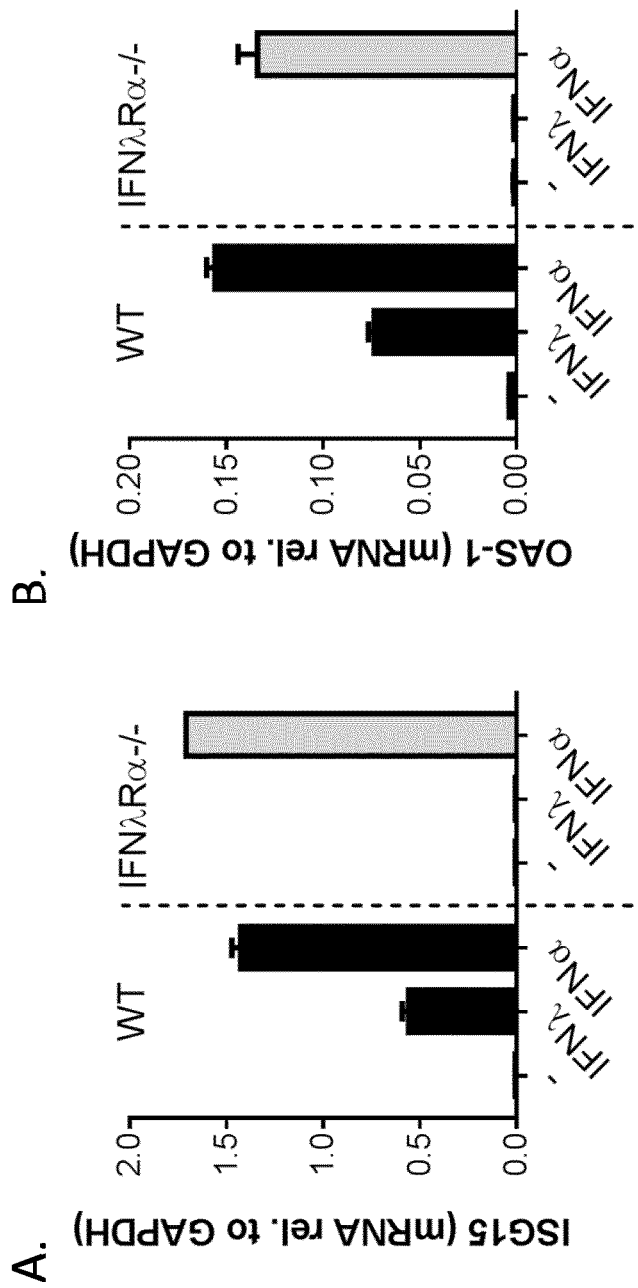

FIG. 19. Recombinant IFNλs Require IFNλRα for Activity

Neutrophils from wild type (WT) C57BL/6 mice and IFNλRα$^{-/-}$ mice were isolated and subjected to 100 ng/ml IFNλ3 or IFNα2 for 4h. Cells were then collected, RNA extracted, cDNA obtained and analyzed for the expression of ISGI5 (A) and OAS1 (B) by qPCR. Data are expressed as mean±SEM of n=2 experiments per group.

DETAILED DESCRIPTION OF THE INVENTION

Definitions

As used herein, the term "activator of IFNλ receptor" refers to any substance, compound or molecule activating IFNλ receptor. IFNλ receptor comprises subunits IL10R2 (CRF2-4) and IFNλR1 (IL28RA, CRF2-12). Activation of IFNλ receptor triggers Janus kinase activation (Jak1 and Tyk2) and phosphorylation and activation of the transcription factors STAT1, STAT2 and STAT3, and interferon-regulated transcription factors IRFs. Upon phosphorylation, STATs translocate into the nucleus to induce hundreds of genes altogether termed IFN-stimulated genes or ISGs. Accordingly, an activator of IFNλ receptor is any substance, compound or molecule triggering these (or other) signaling events via the IFNλ receptor. For example, the activator of IFNλ receptor may be a small molecule, an antibody or an antibody fragment, a peptide, a polynucleotide expressing IFNλ, IFNλ or an IFNλ derivative. An activator of IFNλ receptor may also be an agent that triggers an increase of endogenous IFNλ in a subject after administration of the agent to the subject.

An activator of the IFNλ receptor can also be defined as any substance, compound or molecule activating IFNλR1. This can be tested in cells expressing or lacking IFNλR1 (IL28RA, CRF2-12), the unique alpha subunit of the IFNλ receptor providing ligand specificity and discriminating it from any other receptor complex. For example, this can be tested in human embryonic kidney cells 293 that express IL-10Rβ/CRF2-4 but lack IFNλR1 (HEK293; ATCC) (Hamming O J et al. EMBO J 2013) untransfected or transfected with a plasmid constitutively expressing IFNλR1 (e.g. plasmid with catalogue number RC221789 from OriGine Technologies Inc, MD, USA). Specific response to the IFNλ receptor activator can be determined by examining the activation of downstream signaling such as the phosphorylation of STAT1 by western blotting at 15 and 30 min upon stimulation and/or the induction of Isg15 and Oas1 by qPCR at 6 h upon stimulation. This should be present only in IFNλR1 transfected cells but completely absent in untransfected or mock plasmid-transfected cells.

Whether or not a compound is an activator of the IFNλ receptor can be tested in HEK293-derived cells that stably express the Lucia luciferase secreted reporter gene under the control of the interferon (IFN)-inducible promoter (consisting of the IFN-stimulated genes (ISG) 54 promoter enhanced by a multimeric IFN-stimulated response elements), known as HEK-Lucia™ Null cells (Catalogue code hkl-null; Invivogen, CA, USA). HEK-Lucia™ Null cells can be left untransfected or transfected with a plasmid constitutively expressing IFNλR1 and examined for the induction of luciferase activity at 6 h following stimulation with the IFNλ receptor activator.

Alternatively, an activator of the IFNλ receptor can be examined in THP1-Lucia™ ISG cells expressing the secreted luciferase reporter gene under the control of an IRF-inducible promoter (consisting of five IFN-stimulated response elements fused to an ISG54 minimal promoter) (Catalogue code thpl-isg; Invivogen, CA, USA). THP1-Lucia™ ISG cells do not express IFNλR1 and do not respond to IFNλ unless transfected with IFNλR1. THP1-Lucia™ ISG cells, untransfected or transfected with a plasmid constitutively expressing IFNλR1, can be assessed for the induction of luciferase activity at 6 h following stimulation with the IFNλ receptor activator. Only IFNλR1-expressing THP1-Lucia™ ISG cells should respond to the IFNλ receptor activator.

As used herein, the term "IFNλ" refers to lambda interferons, also known as type III IFNs or IL-28/29. The IFNλ family currently comprises four known members in humans (IFNλ1/IL-29, IFNλ2/IL-28A, IFNλ3/IL-28B and IFNλ4) and two in mice (IFNλ2/IL-28A, IFNλ3/IL-28B). In a preferred embodiment, human IFNλ1 has the amino acid sequence depicted in SEQ ID NO: 1. In a preferred embodiment, human IFNλ2 has the amino acid sequence depicted in SEQ ID NO: 2. In a preferred embodiment, human IFNλ3 has the amino acid sequence depicted in SEQ ID NO: 3 or the amino acid sequence depicted in SEQ ID NO: 4. In a more preferred embodiment, human IFNλ3 has the amino acid sequence depicted in SEQ ID NO: 4. In a preferred embodiment, human IFNλ4 has the amino acid sequence depicted in SEQ ID NO: 5. In a further preferred embodiment, human IFNλ1 comprises the amino acid sequence depicted in SEQ ID NO: 1. In a further preferred embodiment, human IFNλ2 comprises the amino acid sequence depicted in SEQ ID NO: 2. In a further embodiment, human IFNλ3 comprises the amino acid sequence depicted in SEQ ID NO: 3 or the amino acid sequence depicted in SEQ ID NO: 4. In a more preferred embodiment, human IFNλ3 comprises the amino acid sequence depicted in SEQ ID NO: 4. In a further preferred embodiment, human IFNλ4 comprises the amino acid sequence depicted in SEQ ID NO: 5.

The term IFNλ further comprises variants and functional equivalents of IFNλ1/IL-29, IFNλ2/IL-28A, IFNλ3/IL-28B and IFNλ4. By variants substantially similar amino acid sequences are intended. The IFNλ polypeptides in accordance with the present invention may be altered in various ways including amino acid substitutions, deletions, truncations and insertions. They may also undergo posttranslational modification. Novel proteins having properties of interest may be created by combining elements and fragments of IFNλ proteins or their receptors, as well as with other proteins. Methods for such manipulations are generally known in the art. The IFNλ proteins encompass naturally occurring proteins as well as variations and modified forms thereof. Such variants will continue to possess the desired IFNλ activity. Obviously, the mutations that will be made in the DNA encoding the variant must not place the sequence out of reading frame and should preferably not create complementary regions that could produce secondary mRNA structure. Variants of a particular protein sequence will have generally at least about 90%, preferably at least about 95% and more preferably at least about 98% sequence identity to that particular protein sequence as determined by sequence alignment programs. In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, WI). The computer algorithm GAP is used to align the two polypeptides or polynucleotides for which the percent sequence identity is to be determined. The sequences are aligned for optimal matching of their respective amino acids (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually ¹⁄₁₀ times the gap opening penalty), as well as a comparison matrix such as PAM 250 or BLOSUM 62 are used in conjunction with the algorithm.

Interferon lambda-1 [Homo sapiens]
Accession: NP_742152.1
SEQ ID NO: 1
MAAAWTVVLVTLVLGLAVAGPVPTSKPTTTGKGCHIGRFKSLSPQELAS

FKKARDALEESLKLKNWSCSSPVFPGNWDLRLLQVRERPVALEAELALT

LKVLEAAAGPALEDVLQPLHTLHHILSQLQACIQPQPTAGPRPRGRLHH

WLHRLQEAPKKESAGCLEASVTFNLFRLLTRDLKYVADGNLCLRTSTHP

EST

Interferon lambda-2 [Homo sapiens]
Accession: NP_742150.1
SEQ ID NO: 2
MKLDMTGDCTPVLVLMAAVLTVTGAVPVARLHGALPDARGCHIAQFKSL -continued

SPQELQAFKRAKDALEESLLLKDCRCHSRLFPRTWDLRQLQVRERPMAL

EAELALTLKVLEATADTDPALVDVLDQPLHTLHHILSQFRACIQPQPTA

GPRTRGRLHHWLYRLQEAPKKESPGCLEASVTFNLFRLLTRDLNCVASG

DLCV

Interferon lambda-3 isoform 1 [Homo sapiens]
Accession: NP_001333866.1
SEQ ID NO: 3
MKLDMTGDCMPVLVLMAAVLTVTGAVPVARLRGALPDARGCHIAQFKSL

SPQELQAFKRAKDALEESLLLKDCKCRSRLFPRTWDLRQLQVRERPVAL

EAELALTLKVLEATADTDPALGDVLDQPLHTLHHILSQLRACIQPQPTA

GPRTRGRLHHWLHRLQEAPKKESPGCLEASVTFNLFRLLTRDLNCVASG

DLCV

Interferon lambda-3 isoform 2 [Homo sapiens]
Accession: NP_742151.2
SEQ ID NO: 4
MTGDCMPVLVLMAAVLTVTGAVPVARLRGALPDARGCHIAQFKSLSPQE

LQAFKRAKDALEESLLLKDCKCRSRLFPRTWDLRQLQVRERPVALEAEL

ALTLKVLEATADTDPALGDVLDQPLHTLHHILSQLRACIQPQPTAGPRT

RGRLHHWLHRLQEAPKKESPGCLEASVTFNLFRLLTRDLNCVASGDLCV

Interferon lambda-4 [Homo sapiens]
Accession: NP_001263183.2
SEQ ID NO: 5
MRPSVWAAVAAGLWVLCTVIAAAPRRCLLSHYRSLEPRTLAAAKALRDR

YEEEALSWGQRNCSFRPRRDPPRPSSCARLRHVARGIADAQAVLSGLHR

SELLPGAGPILELLAAAGRDVAACLELARPGSSRKVPGAQKRRHKPRRA

DSPRCRKASVVFNLLRLLTWELRLAAHSGPCL

As used herein, the term "IFNλ receptor" refers to a receptor complex comprising subunits IL10Rβ (IL10R2, CRF2-4) and IFNλRα (IFNλR1, IL28RA, CRF2-12). For the activation of the IFNλ receptor, an activator of IFNλ receptor binds IFNλRα which subsequently associates with IL10R3. Accordingly, the IFNλ receptor complex forms sequentially in a two-step binding event. First, the IFNλRα subunit binds to IFNλ with high affinity, which in the second step assemble to the IL-10Rβ subunit, forming the ternary complex at a 1:1:1 IFNλ/IFNλRα/IL-10Rβ stoichiometry. The assembled complex transmits the signal by Janus kinase activation (Jak1 and Tyk2) and phosphorylation and activation of the transcription factors STAT1, STAT2 and STAT3, and interferon-regulated transcription factors IRFs.

As used herein, the term "obesity-related disorders" refers to any disease or condition directly or indirectly linked to overweight and/or obesity. Obesity-related disorders may be inherited or acquired. Preferred, although non-limiting, examples for obesity-related disorders in the sense of the present invention are obesity, hyperphagia, prediabetes, diabetes, insulin resistance, metabolic disease, metabolic syndrome, atherosclerosis, coronary heart disease, carotid artery disease, myocardial infarction, stroke, hyperglycemia, impaired glucose tolerance, beta cell deficiency, non-alcoholic steatotic liver disease, steatosis of the liver, polycystic ovarian syndrome, dyslipidemia, hyperlipidemia, hypercholesterolemia, hyperketonemia, hyperglucagonemia, pancreatitis, pancreatic neoplasms, cardiovascular disease, hypertension, coronary artery disease, renal failure, neuropathy, diabetic retinopathy, cataracts, endocrine disorders, sleep apnea, polycystic ovarian syndrome, neoplasms of the breast, colon, prostate, rectum and ovary, osteoarthritis, hyperuricemia heart failure and cerebrovascular disease.

As used herein, the term "atherosclerosis" refers to a disease affecting arterial blood vessels, involving the hardening (calcification) of arteries, the development of atheromatous plaques within the arteries and the formation of thrombi, triggering thrombotic or thromboembolytic events. Atherosclerosis can be viewed as a problem of wound healing and chronic inflammation. It results in inward or outward remodeling causing blood vessel stenosis and infarction or blood vessel enlargement and aneurysm, respectively. In either case, atherosclerotic plaques can erode or rupture and trigger acute clinical complications such as brain strokes, heart attacks and peripheral artery occlusive diseases in the lower extremities. The pathophysiology of atherosclerosis comprises various important steps, including enhanced endothelial focal adhesiveness, permeability and pro-coagulation (endothelial dysfunction), expression of adhesion molecules, monocyte adhesion and immigration, formation of foam cell and fatty streaks, smooth muscle cell (SMC) migration from the tunica media into the tunica intima, plaque formation and finally, plaque rupture and thrombus formation. A prevalent theme in atherosclerosis is thus the presence of oxidative stress and inflammation, due to the oxidation of LDL and other lipid-rich material.

As used herein, the term "coagulation disorder" refers to conditions wherein increased blood clotting (hypercoagulation) occurs. Increased blood clotting may result in the formation of thrombi, e.g., formation of thrombi in veins, arteries or cardiac chambers. Thrombi can block blood flow at the site of formation. Thrombi can also detach and block distant blood vessels. The coagulation cascade involves>50 mediators with pro- or anti-coagulant activities and is triggered through the activation of platelets and or the induction of tissue factor that activate the contact (intrinsic) and tissue factor (extrinsic) pathways, respectively. Coagulation disorder may be the result of predisposing factors, e.g., genetic mutations. Coagulation disorder may also be a consequence of, e.g., surgery or trauma, prolonged immobilization, medication, obesity or atherosclerosis.

As used herein, the term "obesity" means obese according to any classification system of body weight. Such systems include, but are not limited to, the body mass index (BMI), BMI prime or equivalents. BMI, for example, is an analytical tool used to compare a person's height with their weight, as a rough measure of adiposity. BMI is calculated by dividing a person's mass (in kg) by the height (in m) squared. A human individual is classified as obese, when the BMI value is greater than or equal to 30 (kg/m$^2$). The term "obesity" includes morbid obesity (i.e. BMI greater than or equal to 40 (kg/m$^2$)), childhood obesity and any other kind of obesity in which the subject's BMI is greater than or equal to 30 (kg/m$^2$). Obesity occurs as a result of complex interactions between genes and the environment regulating energy balance, linked pathophysiological processes, and weight. Through a coordinated network of central mechanisms and peripheral signals including sensory nervous system inputs, neuroendocrine axes, and multiple cells and processes within adipose tissue, stomach, pancreas and liver, food intake and energy expenditure are controlled and can lead to excess adiposity, weight gain and diverse metabolic and physiological effects.

As used herein, the term "overweight" means overweight according to any classification system of body weight. An individual is classified as overweight, per BMI for example, when their BMI value is equal to or greater than 25.

As used herein, the term "diabetes" refers to any disease characterized by a high concentration of blood glucose (hyperglycemia). For example, diabetes is diagnosed by demonstrating any one of the following: (i) a fasting plasma glucose level at or above 126 mg/dL (7.0 mmol/l), (ii) a plasma glucose at or above 200 mg/dL (11.1 mmol/l) two hours after a 75 g oral glucose load as in a glucose tolerance test or (iii) symptoms of hyperglycemia and casual plasma glucose at or above 200 mg/dL (11.1 mmol/l). As used herein, the term diabetes refers to "type 1 diabetes" also known as childhood-onset diabetes, juvenile diabetes and insulin-dependent diabetes. As used herein, the term diabetes also refers to "type 2 diabetes" also known as adult-onset diabetes, obesity-related diabetes and non-insulin-dependent diabetes. As used herein, the term diabetes also refers to other forms of diabetes including gestational diabetes, insulin-resistant type 1 diabetes (or "double diabetes"), latent autoimmune diabetes of adults and maturity onset diabetes of the young, which is a group of several single gene (monogenic) disorders with strong family histories that present as type 2 diabetes before 30 years of age.

As used herein, the term "insulin resistance" refers to a condition wherein the cells of the body, in particular muscle, fat and liver cells, fail to effectively respond to insulin. Accordingly, the pancreas increases insulin production. Excess weight also contributes to the development of insulin resistance, as excess fat interferes with the body's ability to use insulin. Lack of exercise further reduces the body's ability to use insulin. Further risk factors for developing insulin resistance include genetic factors, hypertension, age and lifestyle.

As used herein, the term "metabolic syndrome" or "metabolic disease" refers to the physiological condition in mammals that is typically characterized by obesity, insulin resistance, hyperlipidemia and hypertension. It may further encompass vascular abnormalities such as endothelial dysfunction, vascular pro-inflammatory condition and vascular pro-coagulative and pro-thrombotic conditions. Metabolic syndrome also refers to syndromes accompanied by health risk factors such as hypertriglyceridemia, hypertension, carbohydrate metabolism disorders, blood coagulation disorders and obesity. Metabolic syndrome may also include glucose intolerance, dyslipidemia with elevated triglycerides, low HDL-cholesterol, microalbuminuria, predominance of small dense LDL-cholesterol particles, endothelial dysfunction, oxidative stress, inflammation and related disorders of polycystic ovarian syndrome, fatty liver disease and gout. Metabolic disease or metabolic syndrome is a suspected precursor to a wide range of diseases, including type 2 diabetes, cardiovascular disease, stroke, cancer, polycystic ovary syndrome, gout and asthma.

As used herein, the term "dyslipidemia" refers to abnormal levels of lipids (e.g., triglycerides, cholesterol and/or fat phospholipids) in the blood. Dyslipidemia in the sense of the present invention is in particular hyperlipidemia.

As used herein, the term "hyperlipidemia" refers to abnormally elevated levels of any or all lipids and/or lipoproteins in the blood. Hyperlipidemias may basically be classified as either familial (also called primary) caused by specific genetic abnormalities, or acquired (also called secondary) when resulting from another underlying disorder that leads to alterations in plasma lipid and lipoprotein metabolism. Also, hyperlipidemia may be idiopathic, that is, without known cause. Hyperlipidemias are also classified according to which types of lipids are elevated, that is hypercholesterolemia, hypertriglyceridemia or both in combined hyperlipidemia. Elevated levels of Lipoprotein (a) may also be classified as a form of hyperlipidemia.

As used herein, "hypercholesterolemia" refers to the presence of abnormally high levels of cholesterol in the blood. It is a form of high blood lipids and "hyperlipoproteinemia" (elevated levels of lipoproteins in the blood). Elevated levels of non-HDL cholesterol and LDL in the blood may be a consequence of diet, obesity, inherited (genetic) diseases (such as LDL receptor mutations in familial hypercholesterolemia), or the presence of other diseases such as diabetes and an underactive thyroid.

As used herein, "cardiovascular disorder" or "cardiovascular disease" refers to conditions involving the heart and/or blood vessels. Cardiovascular disease includes, but is not limited to, coronary artery diseases, stroke, heart failure, hypertensive heart disease, rheumatic heart disease, cardiomyopathy, heart arrhythmia, congenital heart disease, valvular heart disease, carditis, aortic aneurysms, peripheral artery disease, and venous thrombosis.

As used herein, "coronary heart disease" refers to is a group of diseases that includes: stable angina, unstable angina, myocardial infarction, and sudden cardiac death. It belongs to the group of cardiovascular diseases. Risk factors for developing coronary heart disease include: high blood pressure, smoking, diabetes, lack of exercise, obesity, high blood cholesterol, poor diet, and excessive alcohol.

Medical Uses and Methods of Treatment or Prevention

In one embodiment of the invention, an activator of IFNλ receptor for use in the treatment of obesity-related disorders is provided. Further provided is a method of treating an obesity-related disorder comprising administering a therapeutically effective amount of an activator of IFNλ receptor to a subject in need of such treatment. In another embodiment, an activator of IFNλ receptor for use in the prevention of obesity-related disorders is provided. Further provided is a method for preventing an obesity-related disorder comprising administering a therapeutically effective amount of an activator of IFNλ receptor to a subject in need of such prevention.

In one embodiment, the obesity-related disorder is obesity, hyperphagia, prediabetes, diabetes (including type 1 diabetes, type 2 diabetes, and gestational diabetes), insulin resistance, metabolic disease, metabolic syndrome, atherosclerosis, coronary heart disease, carotid artery disease, myocardial infarction, stroke, thrombosis, coagulation, dyslipidemia, hyperlipidemia or hypercholesterolemia.

The Present Invention Inter Alia Encompasses the Following Items:

1. An activator of IFNλ receptor for use in the prevention or treatment of an obesity-related disorder in a subject.
2. A method of preventing or treating an obesity-related disorder in a subject comprising administering a therapeutically effective amount of an activator of IFNλ receptor to the subject in need of such treatment or prevention.
3. The activator of IFNλ receptor for the use or the method of item 1 or item 2, wherein the obesity-related disorder is selected from the group consisting of obesity, hyperphagia, prediabetes, diabetes (including type 1 diabetes, type 2 diabetes, and gestational diabetes), insulin resistance, metabolic disease, metabolic syndrome, coronary heart disease, carotid artery disease, myocardial infarction, stroke, thrombosis, dyslipidemia, hyperlipidemia or hypercholesterolemia.
4. The activator of IFNλ receptor for the use or the method of item 3, wherein the obesity-related disorder is obesity.
5. The activator of IFNλ receptor for the use or the method of item 3, wherein the diabetes is type 1 diabetes or type 2 diabetes.
6. An activator of IFNλ receptor for use in the therapeutic reduction of body weight in a subject.
7. A method for therapeutic reduction of body weight in a subject comprising administering an activator of IFNλ receptor to the subject.
8. An activator of IFNλ receptor for use in the therapeutic reduction of overweight in a subject.
9. A method for therapeutic reduction of overweight in a subject comprising administering an activator of IFNλ receptor to the subject.
10. Use of an activator of IFNλ receptor for the non-therapeutic reduction of body weight in a subject, optionally wherein the non-therapeutic reduction of body weight involves the suppression of appetite and/or the suppression of overeating.
11. A method for non-therapeutic reduction of body weight in a subject comprising administering an activator of IFNλ receptor to the subject, optionally wherein the non-therapeutic reduction of body weight involves the suppression of appetite and/or the suppression of overeating.
12. Use of an activator of IFNλ receptor for the non-therapeutic reduction of overweight in a subject, optionally wherein the non-therapeutic reduction of overweight involves the suppression of appetite and/or the suppression of overeating.
13. A method for non-therapeutic reduction of overweight in a subject comprising administering an activator of IFNλ receptor to the subject, optionally wherein the non-therapeutic reduction of overweight involves the suppression of appetite and/or the suppression of overeating.
14. The activator of IFNλ receptor for the use, the use, or the method of any one of items 1-13, wherein the subject is a mammalian subject.
15. The activator of IFNλ receptor for the use, the use, or the method of any one of items 1-13, wherein the subject is a human.
16. The activator of IFNλ receptor for the use, the use, or the method of any one of items 1-15, wherein the activator of IFNλ receptor is administered in combination with one or more further therapeutic agent(s).
17. The activator of IFNλ receptor for the use, the use, or the method of item 16, wherein the further therapeutic agent(s) is/are selected from the group consisting of insulin, metformin (Glucophage), meglitinides (Prandin and Starlix), sulfonylureas (glyburide/DiaBeta, glipizide/Glucotrol and Glimepiride/Amaryl), canagliflozin (Invokana) and dapagliflozin (Farxiga), thiazolidinediones, such as pioglitazone (Actos), acarbose (Precose), pramlintide (Symlin), exenatide (Byetta), liraglutide (Victoza), long-acting exenatide (Bydureon), albiglutide (Tanzeum), dulaglutide (Trulicity), DPP-IV inhibitors (sitagliptin, saxagliptin, linagliptin), phentermine, diethylpropion, phendimetrazine, benzphetamine, oxyntomodulin, fluoxetine hydrochloride, qnexa (topiramate and phentermine), excalia (bupropion and zonisamide), contrave (bupropion and naltrexone), xenical (Orlistat), cetilistat, and GT 389-255, statins, cholesterol lowering drugs such as proprotein convertase subtilisin kexin type 9 (PCSK9) inhibitors, ACE inhibitors, aldosterone inhibitors, angiotensin II receptor blockers, beta-blockers, calcium channel blockers, antiplatelets such as aspirin, clopidogrel (Plavix) or dipyridamole (Persantine), anti-coagulants such as warfarin (Coumadin), heparin, direct factor Xa inhibitors, direct thrombin inhibitors, hydralazine, diuretics, corticosteroids, non-steroidal anti-inflammatory drugs, anti-TNF, anti-IL-1 and anti-IL-6.

18. The activator of IFNλ receptor for the use, the use, or the method of any one of items 1-17, wherein the activator of IFNλ receptor is a small molecule, an antibody or an antibody fragment, a peptide, a polynucleotide expressing IFNλ, IFNλ or an IFNλ derivative.

19. The activator of IFNλ receptor for the use, the use, or the method of item 18, wherein the activator of IFNλ receptor is IFNλ.

20. The activator of IFNλ receptor for the use, the use, or the method of item 19, wherein the IFNλ is human IFNλ.

21. The activator of IFNλ receptor for the use, the use, or the method of item 20, wherein the IFNλ is selected from the group consisting of IFNλ1, IFNλ2, IFNλ3 and IFNλ4.

22. The activator of IFNλ receptor for the use, the use, or the method of item 21, wherein the IFNλ is IFNλ1.

23. The activator of IFNλ receptor for the use, the use, or the method of item 21, wherein the IFNλ is IFNλ2.

24. The activator of IFNλ receptor for the use, the use, or the method of item 21, wherein the IFNλ is IFNλ3.

25. The activator of IFNλ receptor for the use, the use, or the method of item 21, wherein the IFNλ is IFNλ4.

26. The activator of IFNλ receptor for the use, the use, or the method of any one of items 19-25, wherein a mammal is treated with homologous IFNλ.

27. The activator of IFNλ receptor for the use, the use, or the method of any one of items 19-26, wherein the IFNλ is pegylated, in particular monopegylated or conjugated with a polyalkyl oxide moiety.

28. The activator of IFNλ receptor for the use, the use, or the method of any one of items 19-27, wherein the IFNλ is administered via intravenous, intraperitoneal, subcutaneous or intramuscular injection; via oral, topical or transmucosal administration; or via nasal or pulmonary inhalation.

29. The activator of IFNλ receptor for the use, the use, or the method of any one of items 19-27, wherein the IFNλ is administered via gene-therapy.

30. The activator of IFNλ receptor for the use, the use, or the method of any one of items 19-29, wherein the IFNλ is administered weekly.

31. The activator of IFNλ receptor for the use, the use, or the method of any one of items 19-29, wherein the IFNλ is administered every two weeks.

32. The activator of IFNλ receptor for the use, the use, or the method of any one of items 19-29, wherein the IFNλ is administered twice a week.

33. The activator of IFNλ receptor for the use, the use, or the method of any one of items 19-32, wherein the IFNλ is administered at a dose of 10 μg to 10 mg.

34. The activator of IFNλ receptor for the use, the use, or the method of item 33, wherein the IFNλ is administered at a dose of 100 μg to 9 mg.

35. The activator of IFNλ receptor for the use, the use, or the method of item 34, wherein the IFNλ is administered at a dose of 500 μg to 8 mg.

36. The activator of IFNλ receptor for the use, the use, or the method of item 35, wherein the IFNλ is administered at a dose of 1 mg to 7 mg.

37. The activator of IFNλ receptor for the use, the use, or the method of item 36, wherein the IFNλ is administered at a dose of 2 mg to 6 mg.

38. The activator of IFNλ receptor for the use, the use, or the method of item 37, wherein the IFNλ is administered at a dose of 5 mg.

39. The activator of IFNλ receptor for the use, the use, or the method of any one of items 19-32, wherein the IFNλ is administered at a dose of 0.1-150 μg/kg body weight.

40. The activator of IFNλ receptor for the use, the use, or the method of item 39, wherein the IFNλ is administered at a dose of 0.5-100 μg/kg body weight.

41. The activator of IFNλ receptor for the use, the use, or the method of item 40, wherein the IFNλ is administered at a dose of 1-90 μg/kg body weight.

42. The activator of IFNλ receptor for the use, the use, or the method of item 41, wherein the IFNλ is administered at a dose of 10-80 μg/kg body weight.

43. The activator of IFNλ receptor for the use, the use, or the method of item 42, wherein the IFNλ is administered at a dose of 20-70 μg/kg body weight.

44. The activator of IFNλ receptor for the use, the use, or the method of item 43, wherein the IFNλ is administered at a dose of 60 μg/kg body weight.

45. A method of determining susceptibility of a subject suffering from an obesity-related disorder to treatment with an activator of IFNλ receptor, wherein the method comprises administering the activator of IFNλ receptor to the subject and determining the effect on the obesity-related disorder.

46. An activator of IFNλ receptor for use in determining susceptibility of a subject suffering from an obesity-related disorder to treatment with the activator of IFNλ receptor, wherein the activator of IFNλ receptor is administered to the subject and the effect on the obesity-related disorder is determined.

47. A pharmaceutical composition comprising an activator of IFNλ receptor and a pharmaceutically acceptable excipient for use in the treatment of an obesity-related disorder.

In one embodiment of the invention, an activator of IFNλ receptor for use in the treatment of atherosclerosis is provided. Further provided is a method of treating atherosclerosis comprising administering a therapeutically effective amount of an activator of IFNλ receptor to a subject in need of such treatment. In another embodiment, an activator of IFNλ receptor for use in the prevention of atherosclerosis is provided. Further provided is a method for preventing atherosclerosis comprising administering a therapeutically effective amount of an activator of IFNλ receptor to a subject in need of such prevention.

In one embodiment, the atherosclerosis is atherosclerosis, Mönckeberg's arteriosclerosis or arteriolosclerosis.

In one embodiment of the invention, an activator of IFNλ receptor for use in the treatment of coagulation disorders is provided. Further provided is a method of treating a coagulation disorder comprising administering a therapeutically effective amount of an activator of IFNλ receptor to a subject in need of such treatment. In another embodiment, an activator of IFNλ receptor for use in the prevention of coagulation disorders is provided. Further provided is a method for preventing coagulation disorders comprising administering a therapeutically effective amount of an activator of IFNλ receptor to a subject in need of such prevention.

In one embodiment, the coagulation disorder is thrombosis, venous thrombosis, deep vein thrombosis, arterial thrombosis, limb ischemia, stroke or myocardial infarction.

In a preferred embodiment, an activator of IFNλ receptor for use in the treatment of obesity is provided.

In another preferred embodiment, an activator of IFNλ receptor for use in the treatment of prediabetes or diabetes (including type 1 diabetes, type 2 diabetes, and gestational diabetes) is provided.

In another preferred embodiment, an activator of IFNλ receptor for use in the treatment of metabolic disease or metabolic syndrome is provided.

In another preferred embodiment, an activator of IFNλ receptor for use in the treatment of coronary heart disease is provided.

In another preferred embodiment, an activator of IFNλ receptor for use in the treatment of stroke is provided.

In another preferred embodiment, an activator of IFNλ receptor for use in the treatment of thrombosis is provided.

In another preferred embodiment, an activator of IFNλ receptor for use in the treatment of hypercholesterolemia is provided.

In a preferred embodiment, an activator of IFNλ receptor for use in the prevention of obesity is provided.

In another preferred embodiment, an activator of IFNλ receptor for use in the prevention of prediabetes or diabetes (including type 1 diabetes, type 2 diabetes, and gestational diabetes) is provided.

In another preferred embodiment, an activator of IFNλ receptor for use in the prevention of metabolic disease or metabolic syndrome is provided.

In another preferred embodiment, an activator of IFNλ receptor for use in the prevention of coronary heart disease is provided.

In another preferred embodiment, an activator of IFNλ receptor for use in the prevention of stroke is provided.

In another preferred embodiment, an activator of IFNλ receptor for use in the prevention of thrombosis is provided.

In another preferred embodiment, an activator of IFNλ receptor for use in the prevention of hypercholesterolemia is provided.

Also provided in a preferred embodiment of the present invention is an activator of IFNλ receptor for use for the reduction of atheromatic plaque formation and rupture.

Also provided in a preferred embodiment of the present invention is an activator of IFNλ receptor for use for the prevention of atheromatic plaque formation and rupture.

Further conditions that can be treated or prevented with an activator of IFNλ receptor in accordance with the invention include, but are not limited to, hyperglycemia, impaired glucose tolerance, beta cell deficiency, non-alcoholic steatotic liver disease, steatosis of the liver, hyperlipidemia, dyslipidemia, hyperketonemia, hyperglucagonemia, pancreatitis, pancreatic neoplasms, cardiovascular disease, hypertension, coronary artery disease, renal failure, neuropathy, diabetic retinopathy, cataracts, endocrine disorders, sleep apnea, polycystic ovarian syndrome, neoplasms of the breast, colon, prostate, rectum and ovary, osteoarthritis, hyperuricemia heart failure and cerebrovascular disease.

Also, according to the present invention an activator of IFNλ receptor can be used in regulating insulin responsiveness in a patient. In one embodiment, an activator of IFNλ receptor restores insulin sensitivity or responsiveness. In a further embodiment, an activator of IFNλ receptor generates insulin sensitivity or responsiveness. In another embodiment, an activator of IFNλ receptor increases glucose uptake by a cell.

Further provided in accordance with the present invention is the use of an activator of IFNλ receptor for the non-therapeutic reduction of body weight. Such reduction of weight may be achieved by the suppression of appetite. Also, such reduction of weight may be achieved by the reduction of overeating. In one embodiment, a use of an activator of IFNλ receptor for the reduction of weight in an individual is provided. In a further embodiment, a use of an activator of IFNλ receptor for maintaining a certain weight in an individual is provided. Weight maintenance may be desirable after weight loss.

Also provided in accordance with the present invention is an activator of IFNλ receptor for use in the therapeutic reduction of body weight. Such reduction of weight may be achieved by the suppression of appetite. Also, such reduction of weight may be achieved by the reduction of overeating. In one embodiment, an activator of IFNλ receptor for use in the therapeutic reduction of weight in an individual is provided. In a further embodiment, an activator of IFNλ receptor for use in maintaining a certain weight in an individual is provided. Weight maintenance may be desirable after weight loss.

Also provided is a method for the reduction of body weight in a subject, comprising administering an effective amount of an activator of IFNλ receptor to the subject. Such reduction of weight may be achieved by the suppression of appetite. Also, such reduction of weight may be achieved by the reduction of overeating. In one embodiment, a method for the reduction of weight in an individual is provided, comprising administering an effective amount of an activator of IFNλ receptor to the subject. Further provided is a method for maintaining weight in an individual, comprising administering an effective amount of an activator of IFNλ receptor to the subject. Weight maintenance may be desirable after weight loss.

The patients or subjects to be treated, analyzed or diagnosed in accordance with the methods and uses of the present invention may be any kind of mammals, such as mice, rats, hamsters, guinea pigs, cats, dogs, horses, monkeys, camels, lamas, lions, tigers and elephants. In a preferred embodiment, the patient or subject is a human.

In one embodiment, the activator of the IFNλ receptor is a small molecule. In a further embodiment, the activator of the IFNλ receptor is an antibody or an antibody fragment. In another embodiment, the activator of the IFNλ receptor is a peptide. In yet another embodiment, the activator of the IFNλ receptor is a polynucleotide expressing IFNλ. Further, the activator of the IFNλ receptor may be IFNλ or an IFNλ derivative. In one embodiment, the activator of the IFNλ receptor is an agent that triggers an increase of endogenous IFNλ.

In one embodiment, the activator of the IFNλ receptor binds to the IFNλ receptor and triggers Jak1 and Tyk2 activation. In a further embodiment, the activator of the IFNλ receptor binds to the IFNλ receptor and mediates STAT1, STAT2 and/or STAT3 phosphorylation. In another embodiment, the activator of the IFNλ receptor binds to the IFNλ receptor and mediates STAT1, STAT2 and/or STAT3 translocation into the nucleus. In another embodiment, the activator of the IFNλ receptor binds to the IFNλ receptor and mediates gene transcription.

In one embodiment, the activator of IFNλ receptor is IFNλ. The IFNλ may be human IFNλ. In one embodiment, the IFNλ is IFNλ1, in particular human IFNλ1. In a further embodiment, the IFNλ is IFNλ2, in particular human IFNλ2. In another embodiment, the IFNλ is IFNλ3, in particular human IFNλ3. In yet another embodiment, the IFNλ, is IFNλ4, in particular human IFNλ4.

The IFNλ to be used or administered in accordance with the present invention may be derived from any mammalian species. In a preferred embodiment, the IFNλ is homologous with respect to the mammal, i.e., it represents IFNλ from the same species as the mammal to be treated. For example, in one embodiment where the patient or subject is a mouse, murine IFNλ is administered. Further, where the patient or subject is a human, the IFNλ that is used or administered in connection with the treatment or prevention of the present invention is human IFNλ.

IFNλ may be prepared from a number of different sources. For example, recombinant IFNλ can be expressed in a cell using a number of different expression systems (both prokaryotic or eukaryotic) and isolated. Optionally, IFNλ may be fused to a protein tag. Recombinant IFNλ may be expressed, secreted into the supernatant, and IFNλ may then be purified from the supernatant. Methods by which recombinant polypeptide can be expressed and purified from cells are well known in the art. Such methods are disclosed, e.g., in Sambrook et al, Molecular Cloning: A Laboratory Manual. 2001. 3rd edition. IFNλ may also be synthetically synthesized in a cell-free in vitro system. This may use purified RNA polymerase, ribosomes, tRNA and ribonucleotides.

In one embodiment, the IFNλ is conjugated to PEG. In one embodiment, the IFNλ is monopegylated. PEGylation is a method wherein a polypeptide or peptidomimetic compound is modified such that one or more polyethylene glycol (PEG) molecules are covalently attached to the side chain of one or more amino acids or derivatives thereof. It is one of the most important molecule altering structural chemistry techniques (MASC). Other MASC techniques may be used as well. Such techniques may improve the pharmacodynamic properties of the IFNλ, for example increasing the half-life in vivo. A PEG-protein conjugate may be formed by first activating the PEG moiety so that it will react with, and couple to, the protein or peptidomimetic compound. PEG moieties can vary considerably in molecular weight and conformation. PEG2 involves coupling of a 30 kDa (or less) PEG to a lysine amino acid (although PEGylation can be extended to the addition of PEG to other amino acids) that is further reacted to form a branched structure that behaves like a linear PEG of much greater molecular weight (Kozlowski et al., (2001), Biodrugs 15, 419-429). Methods that may be used to covalently attach the PEG molecules to polypeptides are further described in Roberts et al., (2002) Adv. Drug Deliv Rev 54, 459-476, Bhadra et al., (2002) Pharmazie 57, 5-29, Kozlowski et al., (2001) J Control Release 72, 217-224, and Veronese (2001) Biomaterials, 22, 405-417 and references referred to therein. Pegylated IFNλ can also be prepared as described in, e.g., WO 2013028233.

IFNλ may be conjugated to any other suitable moiety. For example, the IFNλ may be conjugated with a polyalkyl oxide moiety.

Diagnostic Uses and Methods

In one embodiment, an activator of IFNλ receptor for use in determining susceptibility of a patient suffering from an obesity-related disorder to treatment with the activator of IFNλ receptor is provided, wherein the activator of IFNλ receptor is administered to the patient and the effect on the obesity-related disorder is determined. Also provided is a method of determining susceptibility of a patient suffering from an obesity-related disorder to treatment with an activator of IFNλ receptor, wherein the method comprises administering the activator of IFNλ receptor to the patient and determining the effect on the obesity-related disorder.

An improvement of the obesity-related disorder indicates that the patient is susceptible to treatment with an activator of IFNλ receptor. Improvement of the obesity-related disorder may be measured using established means, such as determining levels of metabolic compounds in a subject or determining weight loss in a subject.

In one embodiment, an activator of IFNλ receptor for use in determining susceptibility of a patient suffering from atherosclerosis to treatment with the activator of IFNλ receptor is provided, wherein the activator of IFNλ receptor is administered to the patient and the effect on the atherosclerosis is determined. Also provided is a method of determining susceptibility of a patient suffering from atherosclerosis to treatment with an activator of IFNλ receptor, wherein the method comprises administering the activator of IFNλ receptor to the patient and determining the effect on the atherosclerosis.

An improvement of the atherosclerosis indicates that the patient is susceptible to treatment with an activator of IFNλ receptor.

In one embodiment, an activator of IFNλ receptor for use in determining susceptibility of a patient suffering from a coagulation disorder to treatment with the activator of IFNλ receptor is provided, wherein the activator of IFNλ receptor is administered to the patient and the effect on the coagulation disorder is determined. Also provided is a method of determining susceptibility of a patient suffering from a coagulation disorder to treatment with an activator of IFNλ receptor, wherein the method comprises administering the activator of IFNλ receptor to the patient and determining the effect on the coagulation disorder.

An improvement of the coagulation disorder indicates that the patient is susceptible to treatment with an activator of IFNλ receptor.

Modes of Administration

The activator of IFNλ receptor may be formulated as a pharmaceutical composition comprising the activator of IFNλ receptor and a pharmaceutically acceptable excipient. The activator of IFNλ receptor, or the composition comprising the activator of IFNλ receptor, may be employed alone or in combination with further therapeutic agents (combination) for the treatment or prevention of the conditions, or for the diagnostic purposes, described or claimed herein. The further therapeutic agent(s) may be one or more agents that exhibit therapeutic activity in one or more of the metabolic disorders described herein, or the pathological conditions associated therewith. Further therapeutic agents that can be administered in combination with the activator of IFNλ receptor include, but are not limited to, insulin, metformin (Glucophage), meglitinides (Prandin and Starlix), sulfonylureas (glyburide/DiaBeta, glipizide/Glucotrol and Glimepiride/Amaryl), canagliflozin (Invokana) and dapagliflozin (Farxiga), thiazolidinediones such as pioglitazone (Actos), acarbose (Precose), pramlintide (Symlin), exenatide (Byetta), liraglutide (Victoza), long-acting exenatide (Bydureon), albiglutide (Tanzeum), dulaglutide (Trulicity), DPP-IV inhibitors (sitagliptin, saxagliptin, linagliptin), phentermine, diethylpropion, phendimetrazine, benzphetamine, oxyntomodulin, fluoxetine hydrochloride, qnexa (topiramate and phentermine), excalia (bupropion and zonisamide), contrave (bupropion and naltrexone), xenical (Orlistat), cetilistat, and GT 389-255, statins, cholesterol lowering drugs such as proprotein convertase subtilisin kexin type 9 (PCSK9) inhibitors, ACE inhibitors, aldosterone inhibitors, angiotensin II receptor blockers, beta-blockers, calcium channel blockers, antiplatelets such as aspirin, clopidogrel (Plavix) or dipyridamole (Persantine), anti-coagulants such as warfarin (Coumadin), heparin, direct factor Xa inhibitors, direct thrombin inhibitors, hydralazine, diuretics, corticosteroids, non-steroidal anti-inflammatory drugs, anti-TNF, anti-IL-1 and anti-IL-6.

In some embodiments, the compounds or compositions provided herein and the further therapeutic agent or agents are administered together, while in other embodiments, the compounds or compositions provided herein and the additional therapeutic agent or agents are administered separately. When administered separately, administration may occur simultaneously or sequentially, in any order.

The amounts of the compounds or compositions provided herein and the other therapeutic agent(s) and the relative timing of administration will be selected by the skilled artisan in order to achieve the desired combined therapeutic effect. The administration in combination of a compound or composition provided herein with other treatment agents may be in combination by administration concomitantly in a unitary composition including both therapeutic agents or in separate compositions each including one of the therapeutic agents. Alternatively, the combination may be administered separately in a sequential manner wherein one treatment agent is administered first and the other second or vice versa. Such sequential administration may be close in time or remote in time.

The activator of IFNλ receptor, the composition comprising the activator of IFNλ receptor and the combinations can be administered by any route, including intravenous, intraperitoneal, subcutaneous, and intramuscular injection; via oral, topical, transmucosal administration; or via nasal or pulmonary inhalation. Depot injection may likewise be employed. Methods for formulating and delivering polypeptides for various routes of administration are known in the art. See, for example, Pharmaceutical Formulation Development of Peptides and Proteins, Second Edition, Lars Hovgaard, Sven Frokjaer, Marco van de Weert; Nov. 14, 2012 by CRC Press.

Peptides activating IFNλ may be administered via gene therapy. In one embodiment, IFNλ or an IFNλ derivative is administered via gene therapy. A nucleic acid molecule encoding IFNλ or an IFNλ derivative is administered to a patient so that it is delivered into the patient's cells, where the nucleic acid is transcribed and translated into IFNλ polypeptide. Such delivery may be achieved by viral and non-viral methods.

In one embodiment, the compounds and combinations of the invention may be delivered via a miniature device such as an implantable infusion pump which is designed to provide long-term continuous or intermittent drug infusion. Such devices can be used to administer an activator of IFNλ receptor via intravenous, intra-arterial, subcutaneous, intraperitoneal, intrathecal, epidural or intraventricular routes.

Dosing

The activator of the IFNλ receptor may be administered according to any suitable dosing scheme.

The activator of IFNλ receptor, the compositions comprising the activator of IFNλ receptor and the combinations can be administered at various intervals. The dosing intervals are selected in order to achieve the desired therapeutic effect. In case of non-therapeutic uses and methods, the dosing interval is selected in order to achieve the desired effect on weight loss or weight maintenance. In a preferred embodiment, the activator of IFNλ receptor, the compositions comprising the activator of IFNλ receptor and the combinations are administered at a weekly dosing interval.

In a further embodiment, the activator of IFNλ receptor, the compositions comprising the activator of IFNλ receptor and the combinations are administered twice per week. In another embodiment, the activator of IFNλ receptor, the compositions comprising the activator of IFNλ receptor and the combinations are administered every two days. In yet another embodiment, the activator of IFNλ receptor, the compositions comprising the activator of IFNλ receptor and the combinations are administered daily.

In a further embodiment, the activator of IFNλ receptor, the compositions comprising the activator of IFNλ receptor and the combinations are administered every other week. In another embodiment, the activator of IFNFλ receptor, the compositions comprising the activator of IFNλ receptor and the combinations are administered every three weeks. In yet another embodiment, the activator of INFλ receptor, the compositions comprising the activator of IFNλ receptor and the combinations are administered once per month.

The amount of the activator of IFNλ receptor administered is selected in order to achieve the desired therapeutic effect. In case of non-therapeutic uses and methods, the amount of the activator of IFNλ receptor administered is selected in order to achieve the desired effect on weight loss or weight maintenance. The activator of IFNλ receptor may be administered as a fixed dose or as a weight-based dose.

In one embodiment, a fixed dose of 10 μg to 10 mg IFNλ is administered. In a further embodiment, a fixed dose of 100 μg to 9 mg IFNλ is administered. In another embodiment, a fixed dose of 500 μg to 8 mg IFNλ is administered. In yet another embodiment, a fixed dose of 1 mg to 7 mg IFNλ is administered. In a preferred embodiment, a fixed dose of 2 mg to 6 mg IFNλ is administered. In a more preferred embodiment, a fixed dose of 5 mg IFNλ is administered.

In one embodiment, a dose of IFNλ of 0.1 μg/kg body weight to 150 μg/kg body weight is administered. In a further embodiment, a dose of IFNλ of 0.5 μg/kg body weight to 100 μg/kg body weight is administered. In another embodiment, a dose of IFNλ of 1 μg/kg body weight to 90 μg/kg body weight is administered. In a preferred embodiment, a dose of IFNλ of 10 μg/kg body weight to 80 μg/kg body weight is administered. In another preferred embodiment, a dose of IFNλ of 20 μg/kg body weight to 70 μg/kg body weight is administered. In a more preferred embodiment, a dose of IFNλ of 60 μg/kg body weight is administered.

In one embodiment, a dose of 10 μg to 10 mg IFNλ is administered at a weekly dosing interval. In a preferred embodiment, a fixed dose of 2 mg to 6 mg IFNλ is administered at a weekly dosing interval. In a more preferred embodiment, a fixed dose of 5 mg IFNλ is administered at a weekly dosing interval.

In another embodiment, a dose of IFNλ of 0.1 μg/kg body weight to 150 μg/kg body weight is administered at a weekly dosing interval. In a preferred embodiment, a dose of IFNλ of 10 μg/kg body weight to 80 μg/kg body weight is administered at a weekly dosing interval. In a more preferred embodiment, a dose of IFNλ of 60 μg/kg body weight is administered at a weekly dosing interval.

Formulations

The activator of the IFNλ receptor may be present or administered in any suitable formulation.

The IFNλ and the compositions comprising IFNλ provided herein can be lyophilized for storage and reconstituted in a suitable liquid prior to use. The liquid may be sterile water or a suitable sterile solution. Any suitable lyophilization method (e.g., spray drying, cake drying) and/or reconstitution techniques can be employed. In a particular embodiment, the invention provides a composition comprising a lyophilized (freeze dried) IFNλ.

In one embodiment, the lyophilized IFNλ or the lyophilized composition comprising IFNλ is provided together with a liquid suitable for reconstitution and a syringe for injection.

In a further embodiment, a liquid formulation of IFNλ is provided. The liquid formulation may comprise one or more stabilizers. In one embodiment, the liquid formulation is stabilizer-free. According to one aspect, the liquid formulation is stable for a time period of 3 months, preferably 6 months and more preferably 12 months upon storage at 4° C. According to a further aspect, the liquid formulation is stable for a time period of 3 months, preferably 6 months and more preferably 12 months upon storage at room temperature.

In one embodiment, the formulation comprises a carrier protein. The carrier protein may be albumin. The role of albumin as a carrier molecule and its inert nature are desirable properties for use as a carrier and transporter of polypeptides in vivo. In one embodiment, the carrier protein is fused to IFNλ. For example, IFNλ may be fused to albumin. Fusion of the carrier protein, such as albumin, to IFNλ may be achieved by genetic manipulation, such that the DNA coding for the carrier protein, e.g., albumin, or a fragment thereof, is joined to the DNA coding for IFNλ.

In one embodiment, a slow release formulation is provided. Such formulations allow for therapeutically effective amounts of the IFNλ or the composition comprising IFNλ to be delivered into the bloodstream over many hours or days following injection or delivery.

The compounds or compositions may also be administered in an in situ gel formulation. Such formulations typically are administered as liquids which form a gel either by dissipation of the water miscible organic solvent or by aggregation of hydrophobic domains present in the matrix. Non-limiting examples include the FLUID CRYSTAL technology (Camurus) and the SABER technology (Durect), and the formulations described in U.S. Pat. Nos. 5,714,159, 6,413,539, 6,004,573 and 6,117,949.

The present invention also inter alia comprises the following items:

1. An activator of IFNλ receptor for use in the prevention or treatment of atherosclerosis in a subject.
2. A method of preventing or treating atherosclerosis in a subject comprising administering a therapeutically effective amount of an activator of IFNλ receptor to the subject in need of such treatment or prevention.
3. The activator of IFNλ receptor for the use or the method of item 1 or item 2, wherein said treatment or prevention is reduction or prevention of atheromatic plaque formation and rupture, respectively.
4. The activator of IFNλ receptor for the use, the use, or the method of any one of items 1-3, wherein the subject is a mammalian subject.
5. The activator of IFNλ receptor for the use, the use, or the method of any one of items 1-3, wherein the subject is a human.
6. The activator of IFNλ receptor for the use, the use, or the method of any one of items 1-5, wherein the activator of IFNλ receptor is administered in combination with one or more further therapeutic agent(s).
7. The activator of IFNλ receptor for the use, the use, or the method of item 6, wherein the further therapeutic agent(s) is/are selected from the group consisting of insulin, metformin (Glucophage), meglitinides (Prandin and Starlix), sulfonylureas (glyburide/DiaBeta, glipizide/Glucotrol and Glimepiride/Amaryl), canagliflozin (Invokana) and dapagliflozin (Farxiga), thiazolidinediones, such as pioglitazone (Actos), acarbose (Precose), pramlintide (Symlin), exenatide (Byetta), liraglutide (Victoza), long-acting exenatide (Bydureon), albiglutide (Tanzeum), dulaglutide (Trulicity), DPP-IV inhibitors (sitagliptin, saxagliptin, linagliptin), phentermine, diethylpropion, phendimetrazine, benzphetamine, oxyntomodulin, fluoxetine hydrochloride, qnexa (topiramate and phentermine), excalia (bupropion and zonisamide), contrave (bupropion and naltrexone), xenical (Orlistat), cetilistat, and GT 389-255, statins, cholesterol lowering drugs such as proprotein convertase subtilisin kexin type 9 (PCSK9) inhibitors, ACE inhibitors, aldosterone inhibitors, angiotensin II receptor blockers, beta-blockers, calcium channel blockers, antiplatelets such as aspirin, clopidogrel (Plavix) or dipyridamole (Persantine), anti-coagulants such as warfarin (Coumadin), heparin, direct factor Xa inhibitors, direct thrombin inhibitors, hydralazine, diuretics, corticosteroids, non-steroidal anti-inflammatory drugs, anti-TNF, anti-IL-1 and anti-IL-6.
8. The activator of IFNλ receptor for the use, the use, or the method of any one of items 1-7, wherein the activator of IFNλ receptor is a small molecule, an antibody or an antibody fragment, a peptide, a polynucleotide expressing IFNλ, IFNλ or an IFNλ derivative.
9. The activator of IFNλ receptor for the use, the use, or the method of item 8, wherein the activator of IFNλ receptor is IFNλ.
10. The activator of IFNλ receptor for the use, the use, or the method of item 9, wherein the IFNλ is human IFNλ.
11. The activator of IFNλ receptor for the use, the use, or the method of item 10, wherein the IFNλ is selected from the group consisting of IFNλ1, IFNλ2, IFNλ3 and IFNλ4.
12. The activator of IFNλ receptor for the use, the use, or the method of item 11, wherein the IFNλ is IFNλ1.
13. The activator of IFNλ receptor for the use, the use, or the method of item 11, wherein the IFNλ is IFNλ2.
14. The activator of IFNλ receptor for the use, the use, or the method of item 11, wherein the IFNλ is IFNλ3.
15. The activator of IFNλ receptor for the use, the use, or the method of item 11, wherein the IFNλ is IFNλ4.
16. The activator of IFNλ receptor for the use, the use, or the method of any one of items 9-15, wherein a mammal is treated with homologous IFNλ.
17. The activator of IFNλ receptor for the use, the use, or the method of any one of items 9-16, wherein the IFNλ is pegylated, in particular monopegylated or conjugated with a polyalkyl oxide moiety.
18. The activator of IFNλ receptor for the use, the use, or the method of any one of items 9-17, wherein the IFNλ is administered via intravenous, intraperitoneal, subcutaneous or intramuscular injection; via oral, topical or transmucosal administration; or via nasal or pulmonary inhalation.
19. The activator of IFNλ receptor for the use, the use, or the method of any one of items 9-17, wherein the IFNλ is administered via gene-therapy.

20. The activator of IFNλ receptor for the use, the use, or the method of any one of items 9-19, wherein the IFNλ is administered weekly.
21. The activator of IFNλ receptor for the use, the use, or the method of any one of items 9-19, wherein the IFNλ is administered every two weeks.
22. The activator of IFNλ receptor for the use, the use, or the method of any one of items 9-19, wherein the IFNλ is administered twice a week.
23. The activator of IFNλ receptor for the use, the use, or the method of any one of items 9-22, wherein the IFNλ is administered at a dose of 10 µg to 10 mg.
24. The activator of IFNλ receptor for the use, the use, or the method of item 23, wherein the IFNλ is administered at a dose of 100 µg to 9 mg.
25. The activator of IFNλ receptor for the use, the use, or the method of item 24, wherein the IFNλ is administered at a dose of 500 µg to 8 mg.
26. The activator of IFNλ receptor for the use, the use, or the method of item 25, wherein the IFNλ is administered at a dose of 1 mg to 7 mg.
27. The activator of IFNλ receptor for the use, the use, or the method of item 26, wherein the IFNλ is administered at a dose of 2 mg to 6 mg.
28. The activator of IFNλ receptor for the use, the use, or the method of item 27, wherein the IFNλ is administered at a dose of 5 mg.
29. The activator of IFNλ receptor for the use, the use, or the method of any one of items 9-22, wherein the IFNλ is administered at a dose of 0.1-150 µg/kg body weight.
30. The activator of IFNλ receptor for the use, the use, or the method of item 29, wherein the IFNλ is administered at a dose of 0.5-100 µg/kg body weight.
31. The activator of IFNλ receptor for the use, the use, or the method of item 30, wherein the IFNλ is administered at a dose of 1-90 µg/kg body weight.
32. The activator of IFNλ receptor for the use, the use, or the method of item 31, wherein the IFNλ is administered at a dose of 10-80 µg/kg body weight.
33. The activator of IFNλ receptor for the use, the use, or the method of item 32, wherein the IFNλ is administered at a dose of 20-70 µg/kg body weight.
34. The activator of IFNλ receptor for the use, the use, or the method of item 33, wherein the IFNλ is administered at a dose of 60 µg/kg body weight.
35. A method of determining susceptibility of a subject suffering from atherosclerosis to treatment with an activator of IFNλ receptor, wherein the method comprises administering the activator of IFNλ receptor to the subject and determining the effect on the atherosclerosis.
36. An activator of IFNλ receptor for use in determining susceptibility of a subject suffering from atherosclerosis to treatment with the activator of IFNλ receptor, wherein the activator of IFNλ receptor is administered to the subject and the effect on the atherosclerosis is determined.
37. A pharmaceutical composition comprising an activator of IFNλ receptor and a pharmaceutically acceptable excipient for use in the treatment of atherosclerosis

EXAMPLES

Methods
Adenovirus Expressing IFNλ2 and Recombinant IFNλ3
Recombinant replication-deficient E1/E3-deleted adenovirus expressing IFNλ2 (AdIFNλ2) and mock control adenovirus (Ad0) were constructed using the Gateway system (Invitrogen). The IFNλ2 cDNA used has been previously described (Koltsida et al. 2011). Recombinant mouse IFNλ3 was purchased by eBioscience.

Experimental Animals and Treatments

Male Apoe−/− mice (Jackson Laboratories) were fed a normal chow diet containing 18.5% protein and 5.5% fat (Harlan Tekland) and analyzed at various time points as indicated. For the assessment of the in vivo effects of IFNλ, 10-week old male Apoe$^{-/-}$ mice were treated intravenously every three weeks with $5\times10^8$ AdIFNλ2 in 200 µl sterile PBS, Ad0 or vehicle control (PBS) as indicated.

In an alternative approach, 5 µg of recombinant mouse IFNλ3 (eBioscience) in 200 µl of sterile PBS were administered intraperitoneally twice per week to 10-week old male Apoe$^{-/-}$ mice. At the end of the treatment, mice were euthanized and serum and tissues were collected.

For the diet-induced obesity model, male wild type C57BL/6 mice (Jackson Laboratories) were fed a high fat diet containing 26% protein and 35% fat (D12492; Research Diets) from week six of age onwards and analyzed at the timepoints indicated. Treatment involved intraperitoneal administration of 5 µg of recombinant mouse IFNλ3 (eBioscience) bi-weekly from week 6 (prophylactic) or week 10 (therapeutic) onwards.

In another setting, male wild type C57BL/6 mice (Jackson Laboratories) fed a normal chow diet (D12450B; Research Diets) were compared to global IFNλRα$^{-/-}$ mice or CD11c$^+$ cell-specific IFNλRα$^{-/-}$ mice (derived from IFNλRα$^{-/-}$ mice reported in Lin J D et al., 2016) and analyzed at the timepoints indicated.

Serum Measurements

Serum proinsulin C-peptide, insulin, leptin, TNF and MCP-1 levels were measured by the Milliplex Map Mouse Adipokine Magnetic Bead Panel (Merck Millipore).

Glucose Tolerance and Insulin Tolerance Tests

Studies were performed as described by Li et al., 2000 and Tordjman et al., 2001. Glucose tolerance testing (GTT) preceded insulin tolerance testing (ITT) by 1 week. GTT was performed following an overnight fast (accounting for the lower fasting glucose levels as compared with those which followed a 5-hour fast). Mice received an intraperitoneal injection of 10% D-glucose (1 g/kg body weight) for GTT and an intraperitoneal injection of human regular insulin (Eli Lilly and Co.) at a dose of 0.75 U/Kg body weight for ITT. Tail vein blood (5-10 µl) for GTT was assayed for glucose at 0, 20, 40, 60, 90 and 120 minutes and for ITT at 0, 20, 40, 60 and 120 minutes with Bayer's Contour Next Meter (Bayer AG).

Indirect Calorimetry Method

Metabolic measurement was performed using an Oxymax indirect calorimetry system (Columbus Instruments). In short, preweighed mice were housed individually in specifically designed Oxymax calorimeter chambers with ad libitum access to the diet and water for 72 h with a 12 h light/12 h dark cycle in an ambient temperature of 22° C. Mice were singly housed for 2 days prior to transferring into the calorimeter chamber. VO2, VCO2 and rates were determined under Oxymax system settings as follows: air flow, 0.6 l/min, sample flow, 0.5 l/min. The system was calibrated against a standard gas mixture to measure O2 consumed (VO2, ml/kg/h) and CO2 generated (VCO2, ml/kg/h). Metabolic rate, respiratory quotient (ratio of VCO2/VO2, RER), and activity (counts) were evaluated over a 48-h period. Energy expenditure was calculated as the product of the calorific value of oxygen (3.815+1.232×respiratory quotient) and the volume of $O_2$ consumed.

Analysis of Atherosclerotic Lesions

Oil Red O (Sigma-Aldrich) stained serial sections of the aortic valve, spanning a 500 μm area and Sudan V (Sigma-Aldrich) stained entire aortas were analyzed using the Image J software (Wayne Rasband).

Immunofluorescence-Immunohistochemistry

Mouse aortic sinus cryosections were stained with anti-mouse CD68 (clone FA-11; Serotec), alpha smooth muscle actin (clone 1A4, Sigma-Aldrich), or isotype control monoclonal antibodies and counterstained with 4-,6-diamidino-2-phenylindole (DAPI, Molecular Probes). Positive staining areas were quantified by use of the Image J software (Wayne Rasband).

Neutrophil Isolation, Stimulation, qPCR and RNAseq Analysis

For neutrophil isolation, bone marrow cells were flushed from femora and tibiae of WT C57BL/6J male mice and suspensions filtered through a 40 m cell strainer. Neutrophils were purified to >99.7% purity with the EasySep™ Mouse Neutrophil Enrichment Kit (StemCell Technologies), according to the manufacturer's instructions. Purified neutrophils were plated at $1\times10^6$ cells/ml in 24-well plates and left untreated or cultured for 8 h in complete RPMI medium in the presence of 100 ng/ml IFNλ3 or IFNα2 (eBioscience). At the end of the incubation, cells were harvested and total RNA was purified with the RNeasy Micro kit (Qiagen) and quantified on a NanoDrop (Thermo Scientific). qPCR analysis was performed on Roche Lightcycler using primers for ISG15 and OAS1 (Galani et al., 2017). RNA seq libraries were prepared with the TruSeq RNA Library Prep Kit v2 (Illumina) according to the manufacturer's instructions. Quality of the libraries was validated with an Agilent DNA 1000 kit run on an Agilent 2100 Bioanalyzer. Bar-coded cDNA libraries were pooled together in equal concentrations in one pool, and were sequenced on a HiSeq2000 (Illumina) at the Genomics Core Facility of EMBL (Heidelberg, Germany). Samples were then analyzed using standard protocols. Briefly, raw reads were pre-processed using FastQC v.0.11.2 and cutadapt v.1.6, and then mapped to the mouse genome (*Mus musculus* UCSC version mm10) using the TopHat version 2.0.13, Bowtie v.1.1.1 and Samtools version v.1.1. The read count table was produced using HTSeq v.0.6. Normalization and differential expression analysis was performed using R/Bioconductor DESeq2.

Statistical Analysis

Statistical significance of differences was assessed using the parametric Student t test for normally distributed data and the nonparametric Mann-Whitney U (MWW) test for skewed data that deviate from normality.

Example 1. IFNλ Lowers Insulin Levels in the Serum

Figure 1:
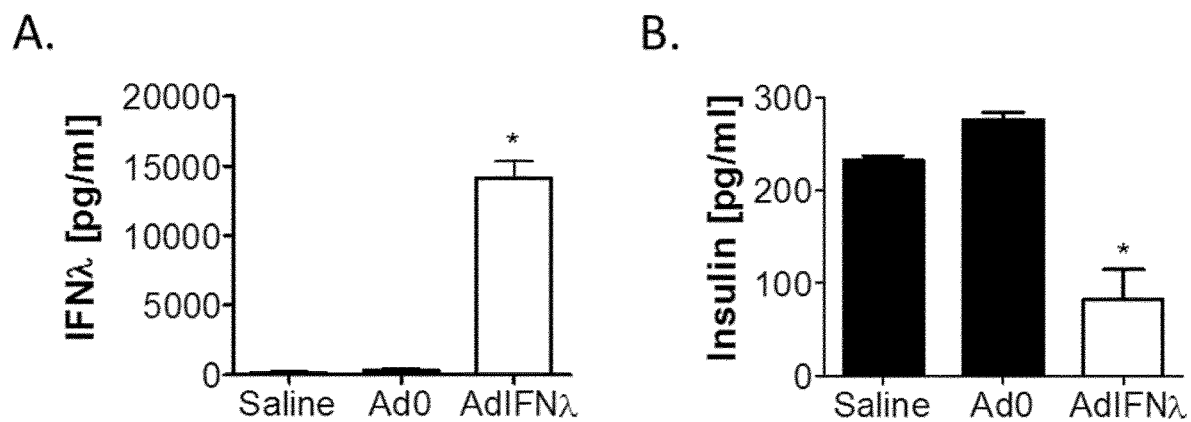
FIG. 1. Systemic Administration of Adenovirally-Expressed IFNλ Lowers Insulin Levels in the Serum 10-week old Apoe$^{-/-}$ mice were treated intravenously with vehicle (PBS), $5 \times 10^8$ mock (Ad0) or $5 \times 10^8$ IFNλ2-expressing adenovirus (AdIFNλ) at day 0 and day 21. Sera were collected and analyzed at day 24. Total levels of IFNλ (A) and insulin (B) in the sera of experimental animals are shown. Data are expressed as mean±SEM of n=3 mice per group. *p<0.05
Figure 2:
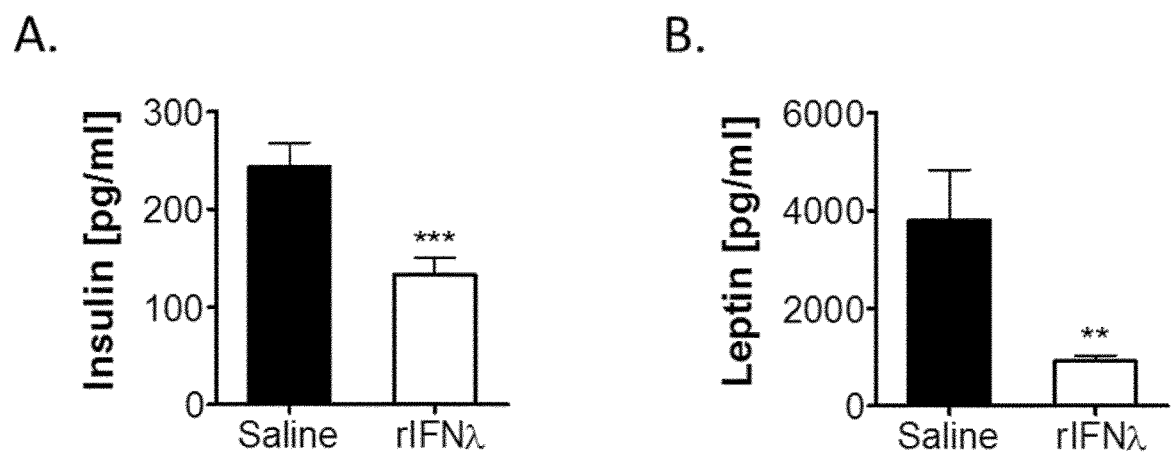
FIG. 2. Systemic Administration of Recombinant IFNλ Lowers Insulin and Leptin Levels in the Serum 10-week old Apoe$^{-/-}$ mice were treated without or with recombinant IFNλ3 (5 μg/mouse), intraperitoneally twice per week for a total of 16 weeks. Control groups received saline. Sera were then collected and analyzed for the presence of insulin (A) and leptin (B). Data are expressed as mean±SEM of n=10-14 mice per group. p<0.01, *p<0.001

Experiments were designed to investigate the effect of IFNλ administration in circulating insulin levels. 10-week old $Apoe^{-/-}$ mice were treated intravenously with vehicle (PBS), $5\times10^8$ mock (Ad0) or $5\times10^8$ IFNλ2-expressing adenovirus (AdIFNλ2) at day 0 and day 21. Sera were collected and analyzed at day 24. The results of these experiments are shown in FIG. 1. AdIFNλ treatment induced high IFNλ levels and markedly reduced insulin levels ($p<0.05$) in the sera of the experimental animals. 10-week old $Apoe^{-/-}$ mice were also treated intraperitoneally twice per week with recombinant IFNλ3 (5 μg/mouse for a total of 16 weeks. Control groups received saline. Sera were then collected and analyzed for the presence of insulin and leptin. As indicated in FIG. 2, recombinant IFNλ3 profoundly reduced circulating insulin and leptin levels ($p<0.05$). As insulin secretion is triggered by increased blood glucose levels and as reduced insulin levels in the circulation indicate improved insulin responsiveness of cells and tissues and improved glucose uptake, these data suggest an important role of IFNλ in body metabolism. The observation that IFNλ treatment also suppresses the production of leptin, a key hormone secreted by adipocytes in direct proportion to the amount of stored body fat with the aim to counteract appetite and increase energy expenditure, further points to a central effect of IFNλ in fat storage and weight gain.

Example 2. IFNλ Promotes Insulin Sensitivity and Enhances Glucose Uptake

Figure 3:
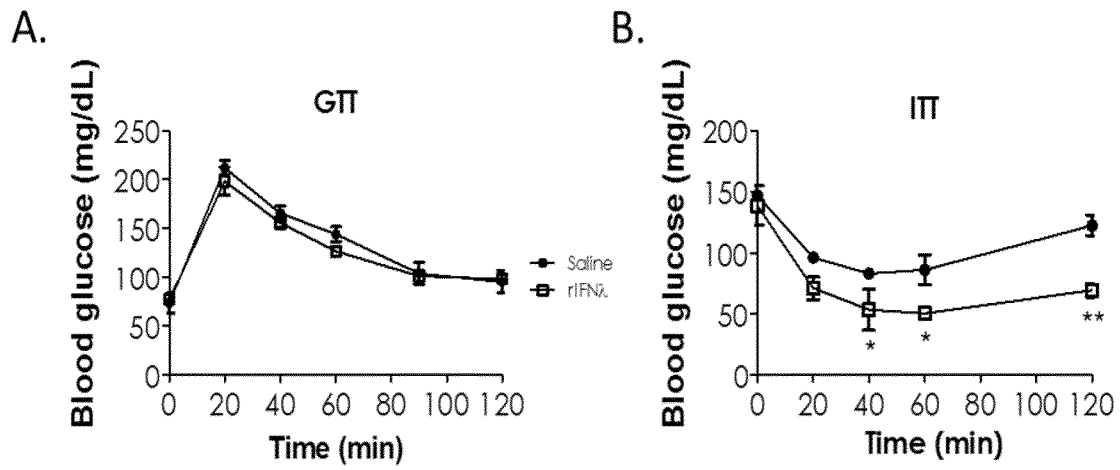
FIG. 3. Recombinant IFNλ restores insulin sensitivity in Apoe-/-mice 10-week old Apoe-/-mice were treated with recombinant IFNλ3 (5 μg/mouse) or saline control, intraperitoneally twice per week for a total of 16 weeks. Control groups received saline. Glucose tolerance testing (OTT) preceded insulin tolerance testing (ITT) by 1 week. GTT was performed following an overnight fast. Mice received an intraperitoneal injection of 10% D-glucose (1 g/kg body weight) for GTT and an intraperitoneal injection of human regular insulin at a dose of 0.75 U/kg body weight for ITT. Tail vein blood (5-10 μl) for GTT was assayed for glucose at 0, 20, 40, 60, 90 and 120 minutes (A) and for ITT at 0, 20, 40, 60 and 120 minutes (B) with Bayer's Contour Next Meter. Data are expressed as mean #SEM of n=3-4 mice per group.*p<0.05, ** p<0.01

In a follow up of Example 1, experiments were designed to investigate the direct effects of IFNλ treatment in insulin sensitivity. 10-week old $Apoe^{-/-}$ mice were treated with recombinant IFNλ3 (5 μg/mouse) or saline control, intraperitoneally twice per week for a total of 16 weeks. Control groups received saline. Glucose tolerance testing (GTT) preceded insulin tolerance testing (ITT) by 1 week. GTT was performed following overnight fasting. Mice received an intraperitoneal injection of 10% D-glucose (1 g/kg body weight) for GTT and an intraperitoneal injection of human regular insulin at a dose of 0.75 U/kg body weight for ITT. Tail vein blood (5-10 μl) for GTT was assayed for glucose at 0, 20, 40, 60, 90 and 120 minutes and for ITT at 0, 20, 40, 60 and 120 minutes with Bayer's Contour Next Meter. Results are shown in FIG. 3. Recombinant IFNλ treatment profoundly improved insulin sensitivity in mice by enhancing glucose uptake following exogenous insulin administration. It is well known that insulin resistance co-exists with obesity. It is also well established that increased insulin levels promote obesity, and obesity in turn drives insulin resistance. This finding therefore provides direct evidence that IFNλ is therapeutically effective in enhancing insulin sensitivity and treating insulin resistance. As insulin resistance promotes obesity, metabolic disease and eventually progresses to diabetes, this finding indicates that IFNλ can also be used to treat or prevent obesity, metabolic disease, diabetes and related comorbidities.

Example 3. IFNλ Prevents Weight Gain in $Apoe^{-/-}$ Mice

Figure 4:
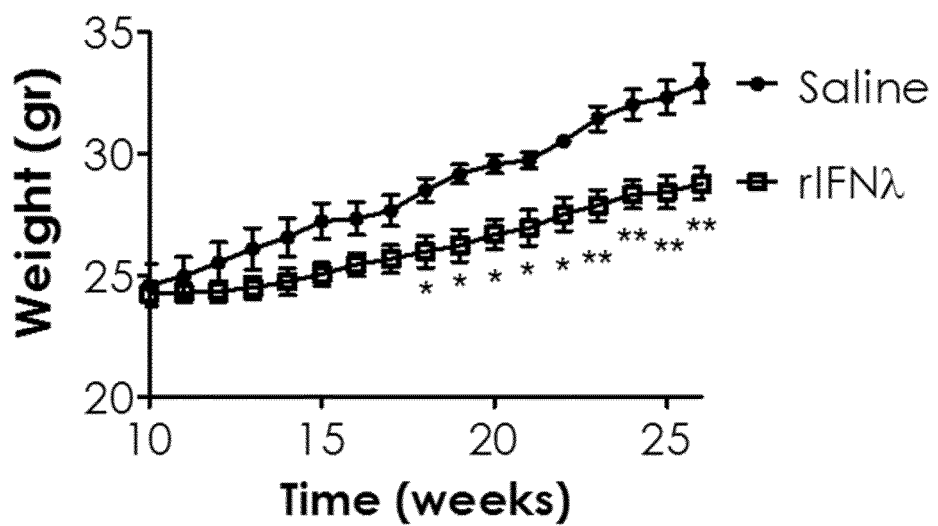
FIG. 4. Recombinant IFNλ Prevents Weight Gain in Apoe$^{-/-}$ Mice 10-week old Apoe$^{-/-}$ mice were treated with recombinant IFNλ3 (5 μg/mouse) twice per week for a total of 16 weeks. Control mice received saline. Weight was measured weakly from week 10 until week 26. Data are expressed as mean±SEM of n=3-5 mice per group. *p<0.05, **p<0.01

To address the effect of IFNλ treatment in weight gain and obesity we used experimental animals. 10-week old $Apoe^{-/-}$ mice were treated with recombinant IFNλ3 (5 μg/mouse) bi-weekly for a total of 16 weeks. The control group of mice received saline. Weight was measured daily from week 10 until week 26. As presented in FIG. 4, recombinant IFNλ treatment significantly inhibited weight gain. These data demonstrate that IFNλ can effectively prevent or treat obesity.

Figure 5:
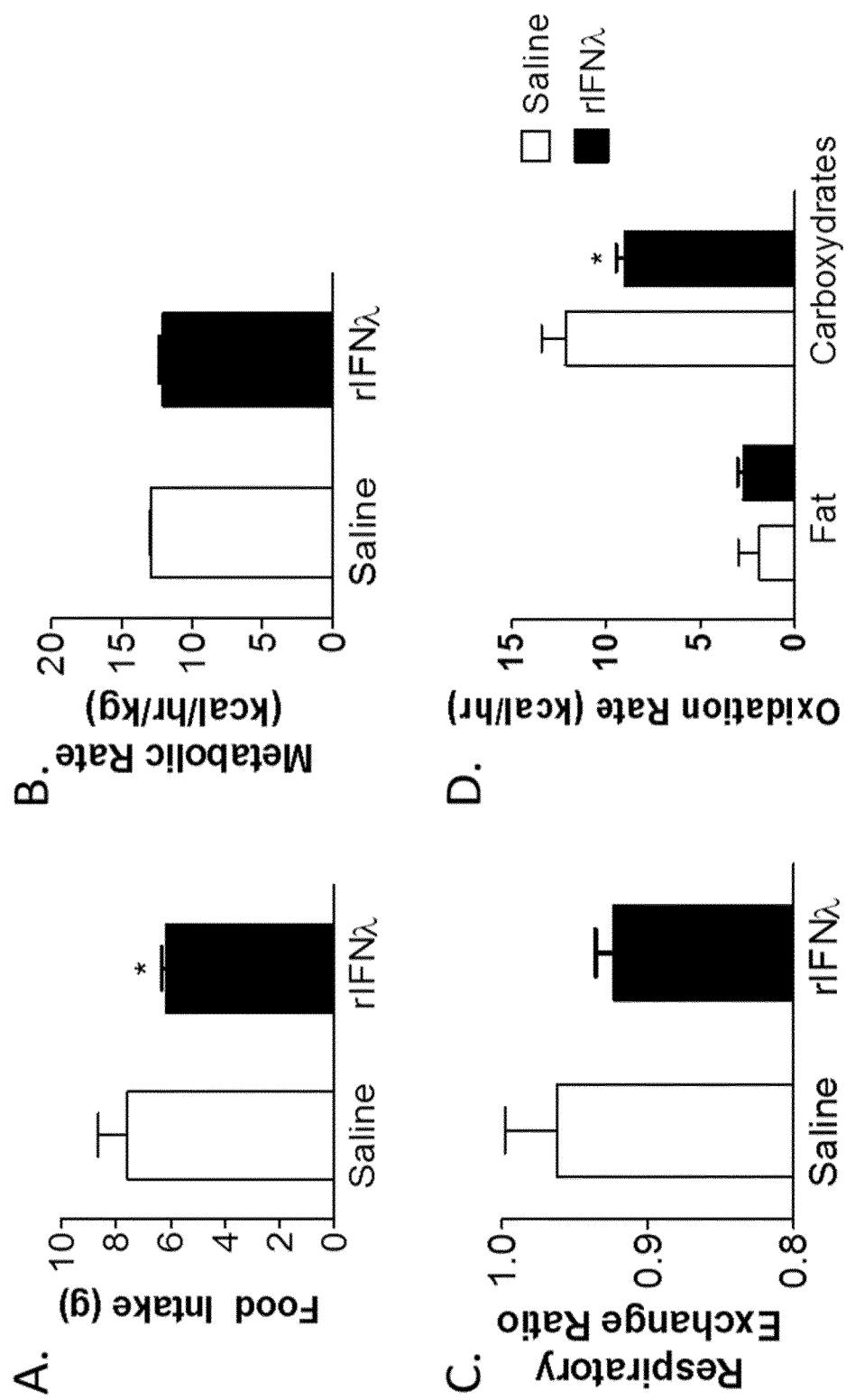
FIG. 5. Recombinant IFNλ Lowers Food Consumption and Reduces the Carbohydrate Burning Rate in Apoe$^{-/-}$ Mice 10-week old Apoe$^{-/-}$ mice were treated with recombinant IFNλ3 (5 μg/mouse) twice per week for a total of 16 weeks. Control mice received saline. Metabolic measurements were performed using an Oxymax indirect calorimetry system according to standard protocols. Food consumption (A), metabolic rate (B), respiratory exchange rate (C) and oxidation rate activity (D) were evaluated over a 48 h period. Data are expressed as mean±SEM of n=3-4 mice per group. *p<0.05

Example 4. IFNλ Lowers Food Consumption and Reduces the Carbohydrate Burning Rate Experiments were performed to shed light into the suppressive effects of IFNλ treatment in weight gain. 10-week old $Apoe^{-/-}$ mice were treated with recombinant IFNλ3 (5 μg/mouse) biweekly for a total of 16 weeks as indicated earlier. Control mice received saline. Metabolic measurements were then performed using an Oxymax indirect calorimetry system according to standard protocols. Food consumption, metabolic rate, respiratory exchange rate and oxidation rate activity were evaluated over a 48 h period. Results are shown in FIG. 5 and reveal a strong effect of recombinant IFNλ treatment in lowering food intake and reducing the consumption of carbohydrates, both key determinants of body weight. These data are in line with the lower weight and reduced circulating insulin and leptin levels of IFNλ treated mice, and demonstrate that IFNλ corrects the imbalance between food intake and energy expenditure and prevents the excessive accumulation of fat.

Figure 6:
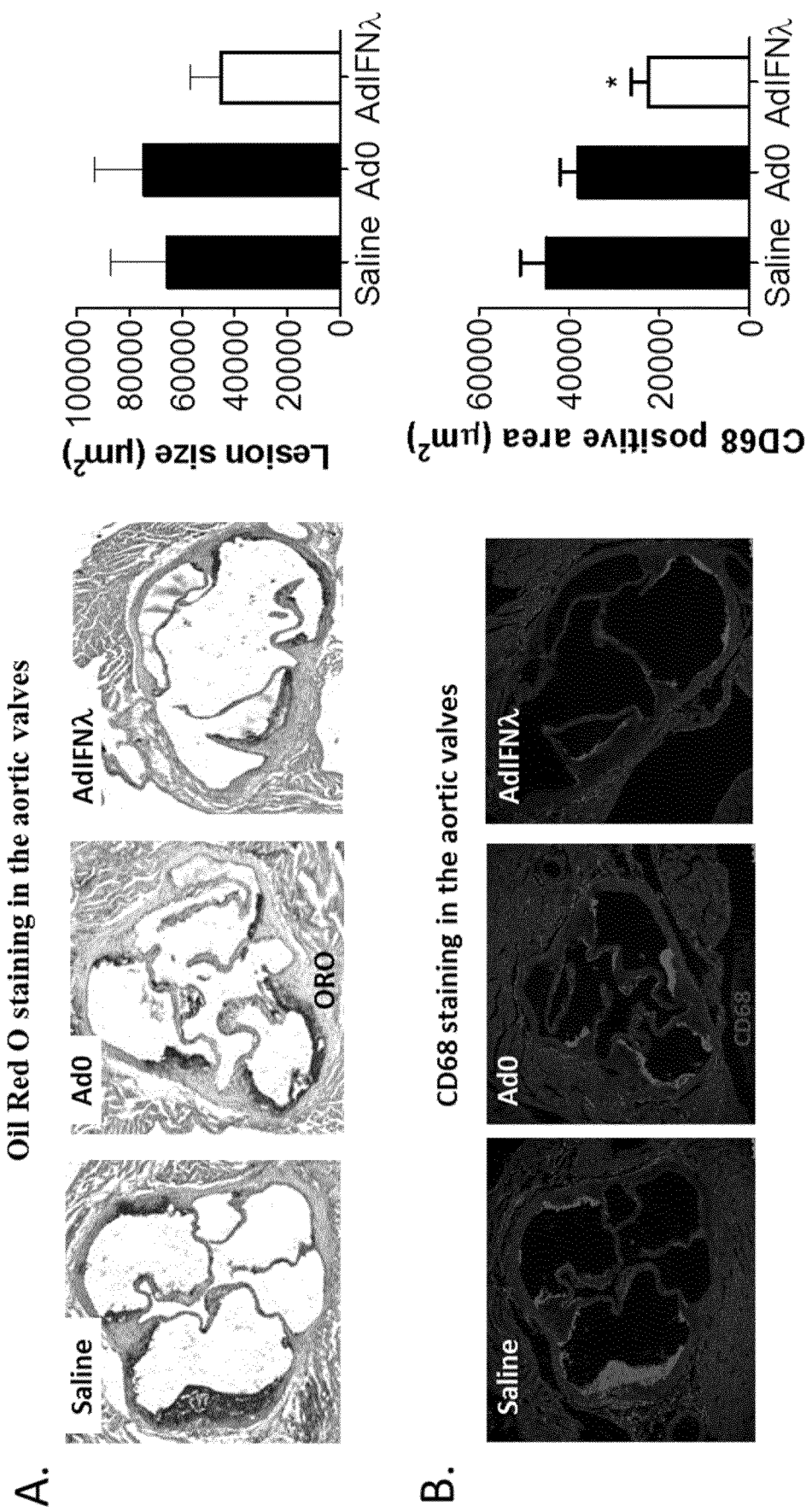
FIG. 6. Systemic Administration of Adenovirally-Expressed IFNλ Reduces Atherosclerosis in Apoe$^{-/-}$ Mice 10-week old Apoe$^{-/-}$ mice were treated intravenously with vehicle (PBS), 5×10$^8$ mock (Ad0) or 5×10$^8$ IFNλ2-expressing adenovirus (AdIFNλ) over 3-week intervals and analyzed for the development of atherosclerosis at 22-weeks. (A) Representative light photomicrographs of ORO-stained sections at the level of the aortic valve and morphometric analysis of lesion size are shown. (B) Representative fluorescence photomicrographs of CD68 and DAPI-stained sections at the level of the aortic valve and morphometric analysis are shown. Data are expressed as mean±SEM of n=4-6 mice per group.*p<0.05
Figure 7:
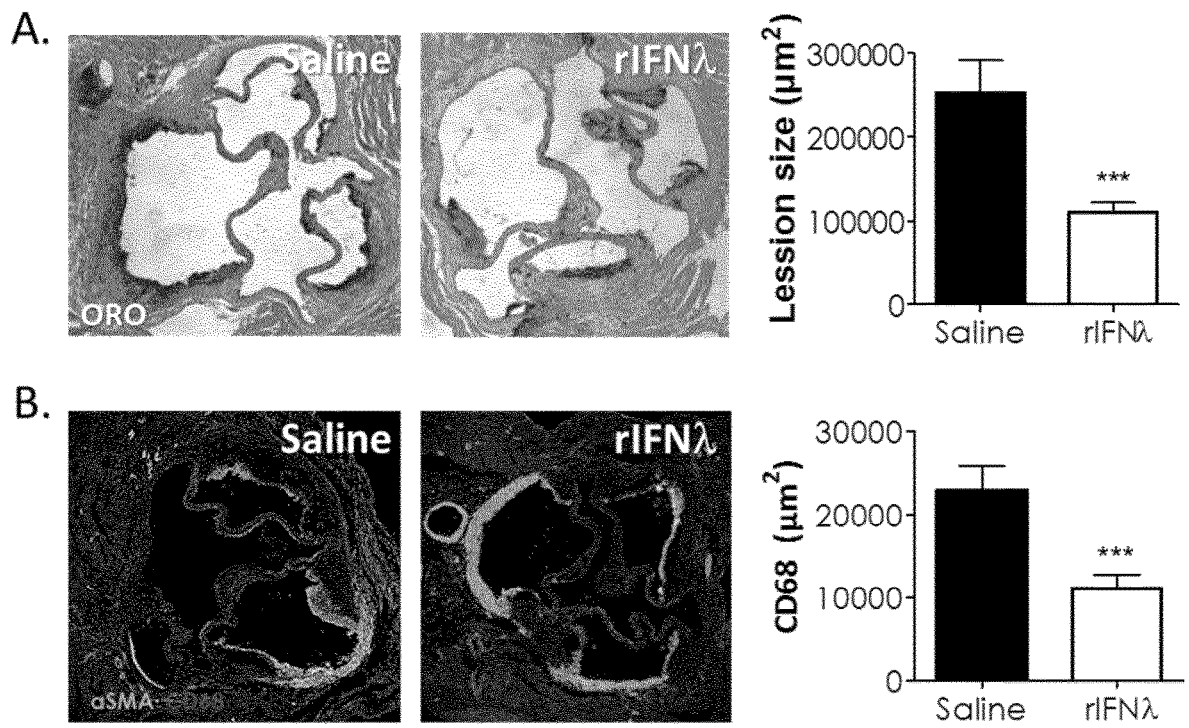
FIG. 7. Recombinant IFNλ Reduces Atherosclerosis in Apoe$^{-/-}$ Mice 10-week old Apoe-/- mice were treated without or with recombinant IFNλ3 (5 μg/mouse), intraperitoneally twice per week for a total of 12 weeks. Control mice received saline. Mice were analyzed for the development of atherosclerosis at 22-weeks. (A) Representative light photomicrographs of ORO-stained sections at the level of the aortic valve and morphometric analysis of lesion size are shown. (B) Representative fluorescence photomicrographs of CD68 and DAPI-stained sections at the level of the aortic valve and morphometric analysis are shown. Data are expressed as mean±SEM of n=10-14 mice per group. ***p<0.001
Figure 8:
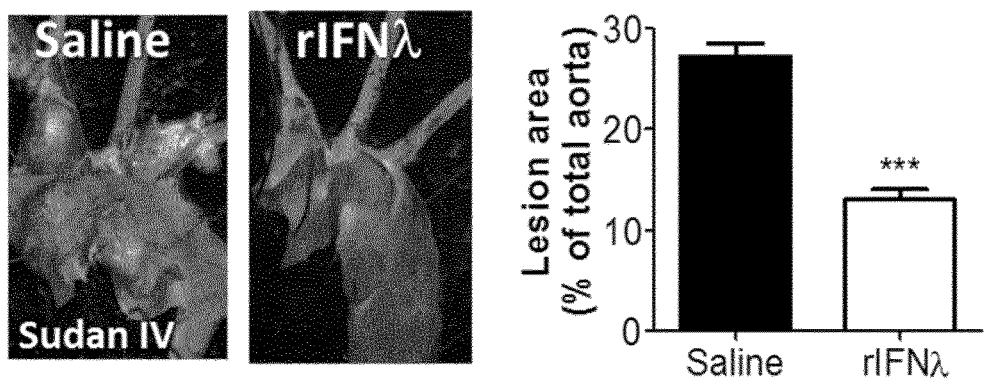
FIG. 8. Recombinant IFNλ Reduces Atherosclerosis in Apoe$^{-/-}$ Mice 10-week old Apoe$^{-/-}$ mice were treated without or with recombinant IFNλ3 (5 μg/mouse), intraperitoneally twice per week for a total of 12 weeks. Control groups received saline. Mice were analyzed for the development of atherosclerosis at 22-weeks by examining macroscopically the aortic arch following staining with Sudan IV. Data are expressed as mean±SEM of n=7-8 mice per group.***p<0.001

Example 5. IFNλ Reduces Atherosclerosis and Prevents Atherosclerotic Plaque Vulnerability 10-week old Apoe$^{-/-}$ mice were treated intravenously with vehicle (PBS), 5×10$^8$ mock (Ad0) or 5×10$^8$ IFNλ2-expressing adenovirus (AdIFNλ) over 3-week intervals for 12 weeks. Alternatively, 10-week old Apoe$^{-/-}$ mice were administered biweekly intraperitoneally recombinant IFNλ3 (5 μg/mouse) for a total of 12 weeks. Control mice received saline. At both cases, mice were analyzed for the development of atherosclerosis at 22-weeks. Representative light photomicrographs of ORO-stained sections and fluorescent photomicrographs of CD68-stained sections at the level of the aortic valve are shown in FIG. 6 and FIG. 7. Results include their respective morphometric analyses. Macroscopic analysis of the aortic arch with Sudan IV staining is shown in FIG. 8. As Apoe$^{-/-}$ mice are the most well established animal model of atherosclerosis, these data demonstrate the potency of IFNλ in treating atherosclerosis by reducing lesion size and macrophage accumulation in the developing atherosclerotic lesions. Moreover, as lipid and CD68$^+$ cell presence indicate a more prone to rupture or 'vulnerable' plaque phenotype, these findings underline the beneficial effects of IFNλ treatment in reducing the risk of atherosclerotic lesions to rupture and give myocardial infarction or stroke.

Example 6. IFNλ Reduces Co-Agulation and Thrombosis

Figure 9:
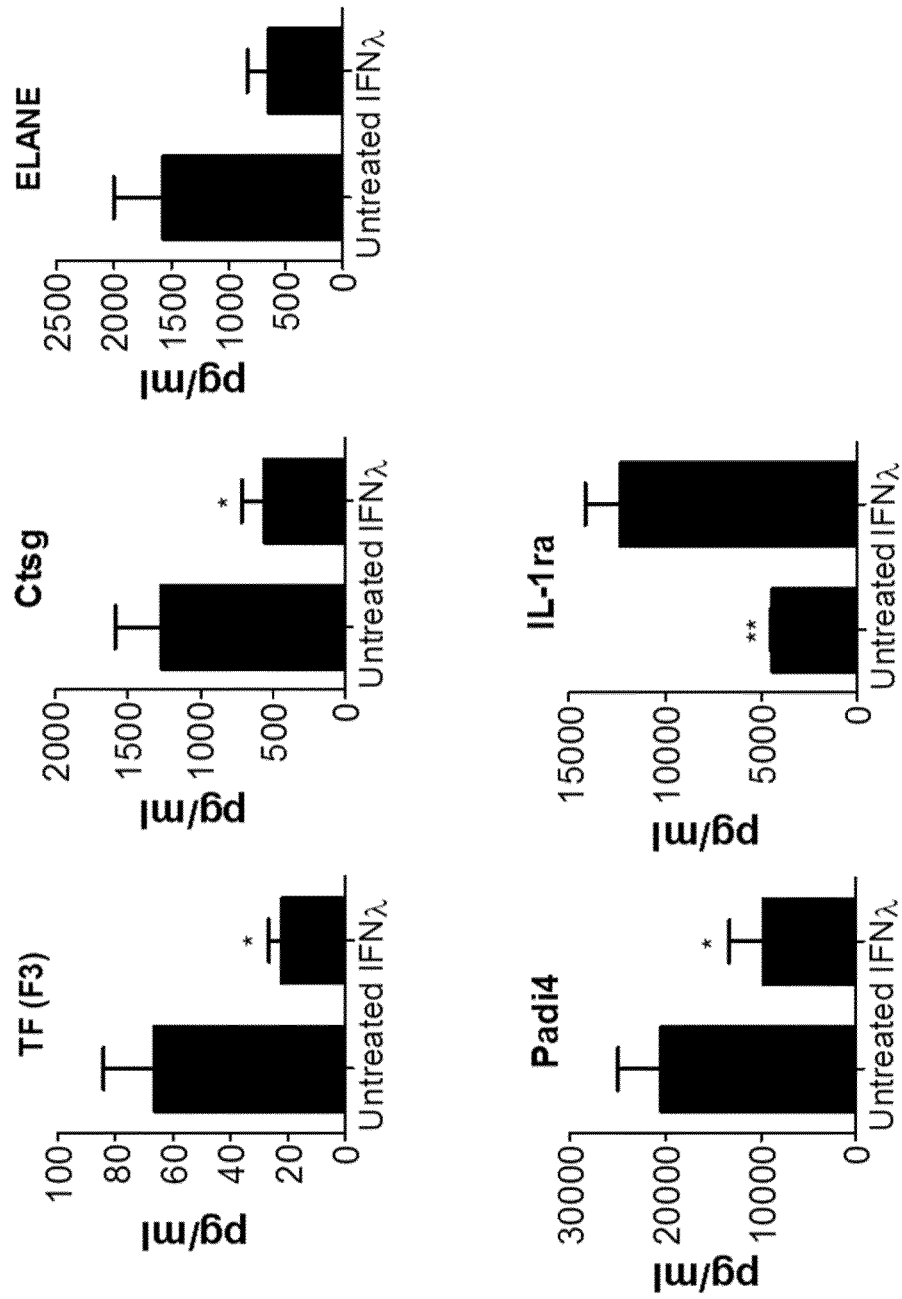
FIG. 9. Recombinant IFNλ Reduces Pro-Coagulant and Pro-Thrombotic Activities

Neutrophils from C57BL/6 mice were isolated to >99% purity and exposed to 100 ng/ml of recombinant IFNλ3 for 8 h. Transcriptional profiling by RNA sequencing was then performed and data analyzed through standard methodologies. IFNλ2 treatment reduces the relative expression levels of tissue factor (TF), Cathepsin G (CTSG), elastase (ELANE), peptidyl arginine deiminase type IV (PADI4) and IL-1ra as shown in FIG. 9. The ability of IFNλ2 to reduce these key mediators involved in co-agulation, neutrophil activation and neutrophil extracellular trap formation, highlights the potency of IFNλ to suppress clot formation and thrombosis.

Figure 11:
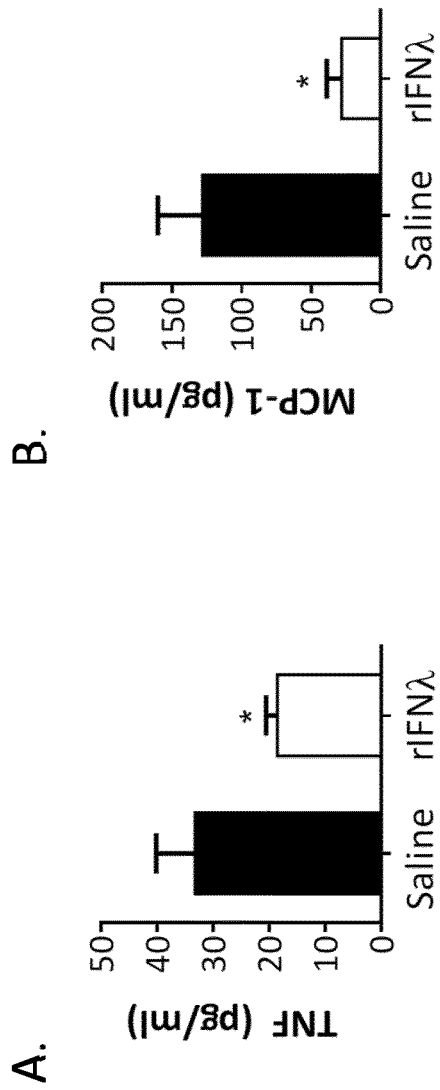
Figure 12:
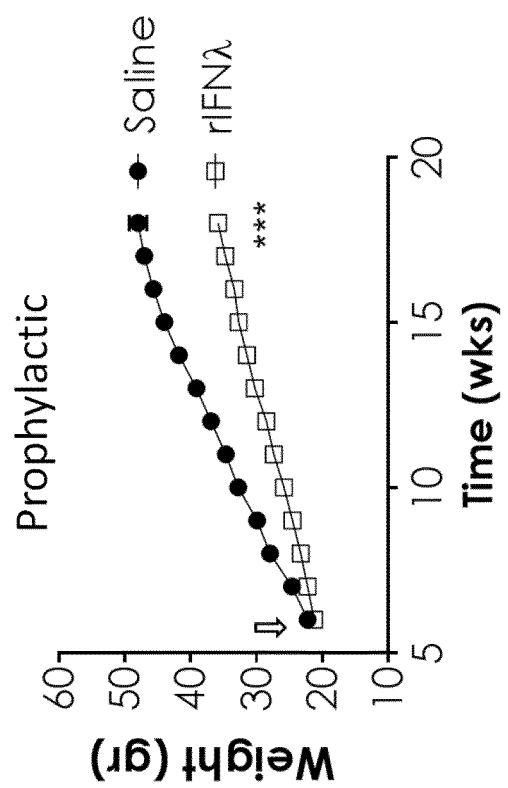

Example 7. IFNλ Reduces Diet-Induced Metabolic and Inflammatory Mediators in C57BL/6 Mice To address the effects of IFNλ treatment in diet-induced metabolic and inflammatory mediators contributing to obesity and insulin resistance, wild type C57BL/6 mice were fed with high fat diet (HFD) from week 6 onwards and treated with recombinant IFNλ3 (5 μg/mouse) twice per week for a total of 8 or 12 weeks. At the end of the treatment period, blood was collected and serum analyzed. As shown in FIG. 10, FIG. 11 and FIG. 13, prophylactic or therapeutic treatment with IFNλ3 markedly reduced the expression of pro-insulin C-peptide, leptin, TNF and MCP-1, indicating that IFNλ3 prevents metabolic dysfunction and systemic inflammation.

Example 8. IFNλ Treats Diet-Induced Obesity and Insulin Resistance in C57BL/6 Mice To address the effects of IFNλ treatment in diet-induced obesity, the most established animal model of obesity, metabolic disease and diabetes, wild type C57BL/6 mice were fed with high fat diet (HFD) from week 6 onwards and treated with recombinant IFNλ3 (5 μg/mouse) twice per week for a total of 8 or 12 weeks. As shown in FIG. 12, FIG. 14 FIG. 15 and FIG. 16, prophylactic or therapeutic treatment with IFNλ3 potently suppressed the development of obesity, reduced food consumption, maintained a healthy body weight and reversed insulin resistance and development of diabetes. This indicates the remarkable therapeutic effect of IFNλ3, and IFNλ receptor activators in general, in preventing obesity, metabolic disease and diabetes.

Example 9. The IFNλ Receptor System is Required for Preserving Normal Weight and Metabolic Health Under Normal Chow Diet To investigate the importance of endogenous IFNλ receptor activators in maintaining a healthy body weight, we used IFNλRα$^{-/-}$ mice lacking IFNλRα globally or in CD11c+ cells only. As shown in FIG. 17 and FIG. 18, global IFNλRα$^{-/-}$ mice and CD11c$^+$ cell-specific IFNλRα$^{-/-}$ mice fed a normal chow diet (NCD) developed an obese phenotype, gaining>20% more weight than wild-type C57BL/6 mice by 26 weeks of age and markedly up-regulating proinsulin C-peptide and leptin levels, an indication of metabolic dysfunction. This demonstrates the importance of the activation of the IFNλ receptor complex for maintaining metabolic health, and further supports the use of IFNλ receptor activators for the treatment of obesity and related diseases.

Example 10. The Activity of Recombinant IFNλs is Dependent on IFNλRα

To confirm the specificity of recombinant IFNλ3 we treated neutrophils from wild type (WT) and IFNλRα$^{-/-}$ mice and examined the induction of downstream signaling. As shown in FIG. 19, IFNλ3 acts indeed through the IFNλ receptor as the induction of its downstream targets ISG15 and OAS1 only takes place in wild type cells whereas IFNα2 can signal in both wild type and IFNλRα$^{-/-}$ mice. This indicates that signaling through IFNλRα is broadly required for maintaining metabolic health and supports the rationale for using IFNλ receptor activators, defined as molecules that require IFNλRα for activity, for the treatment of obesity and obesity-related diseases.

The present invention also inter alia comprises the following items:
1. An activator of IFNλ receptor for use in the prevention or treatment of a coagulation disorder in a subject.
2. A method of preventing or treating a coagulation disorder in a subject comprising administering a therapeutically effective amount of an activator of IFNλ receptor to the subject in need of such treatment or prevention.
3. The activator of IFNλ receptor for the use or the method of item 1 or item 2, wherein the coagulation disorder is thrombosis.

4. The activator of IFNλ receptor for the use, the use, or the method of any one of items 1-3, wherein the subject is a mammalian subject.
5. The activator of IFNλ receptor for the use, the use, or the method of any one of items 1-3, wherein the subject is a human.
6. The activator of IFNλ receptor for the use, the use, or the method of any one of items 1-5, wherein the activator of IFNλ receptor is administered in combination with one or more further therapeutic agent(s).
7. The activator of IFNλ receptor for the use, the use, or the method of item 6, wherein the further therapeutic agent(s) is/are selected from the group consisting of insulin, metformin (Glucophage), meglitinides (Prandin and Starlix), sulfonylureas (glyburide/DiaBeta, glipizide/Glucotrol and Glimepiride/Amaryl), canagliflozin (Invokana) and dapagliflozin (Farxiga), thiazolidinediones, such as pioglitazone (Actos), acarbose (Precose), pramlintide (Symlin), exenatide (Byetta), liraglutide (Victoza), long-acting exenatide (Bydureon), albiglutide (Tanzeum), dulaglutide (Trulicity), DPP-IV inhibitors (sitagliptin, saxagliptin, linagliptin), phentermine, diethylpropion, phendimetrazine, benzphetamine, oxyntomodulin, fluoxetine hydrochloride, qnexa (topiramate and phentermine), excalia (bupropion and zonisamide), contrave (bupropion and naltrexone), xenical (Orlistat), cetilistat, and GT 389-255, statins, cholesterol lowering drugs such as proprotein convertase subtilisin kexin type 9 (PCSK9) inhibitors, ACE inhibitors, aldosterone inhibitors, angiotensin II receptor blockers, beta-blockers, calcium channel blockers, antiplatelets such as aspirin, clopidogrel (Plavix) or dipyridamole (Persantine), anti-coagulants such as warfarin (Coumadin), heparin, direct factor Xa inhibitors, direct thrombin inhibitors, hydralazine, diuretics, corticosteroids, non-steroidal anti-inflammatory drugs, anti-TNF, anti-IL-1 and anti-IL-6.
8. The activator of IFNλ receptor for the use, the use, or the method of any one of items 1-7, wherein the activator of IFNλ receptor is a small molecule, an antibody or an antibody fragment, a peptide, a polynucleotide expressing IFNλ, IFNλ or an IFNλ derivative.
9. The activator of IFNλ receptor for the use, the use, or the method of item 8, wherein the activator of IFNλ receptor is IFNλ.
10. The activator of IFNλ receptor for the use, the use, or the method of item 9, wherein the IFNλ is human IFNλ.
11. The activator of IFNλ receptor for the use, the use, or the method of item 10, wherein the IFNλ is selected from the group consisting of IFNλ1, IFNλ2, IFNλ3 and IFNλ4.
12. The activator of IFNλ receptor for the use, the use, or the method of item 11, wherein the IFNλ is IFNλ1.
13. The activator of IFNλ receptor for the use, the use, or the method of item 11, wherein the IFNλ is IFNλ2.
14. The activator of IFNλ receptor for the use, the use, or the method of item 11, wherein the IFNλ is IFNλ3.
15. The activator of IFNλ receptor for the use, the use, or the method of item 11, wherein the IFNλ is IFNλ4.
16. The activator of IFNλ receptor for the use, the use, or the method of any one of items 9-15, wherein a mammal is treated with homologous IFNλ.
17. The activator of IFNλ receptor for the use, the use, or the method of any one of items 9-16, wherein the IFNλ is pegylated, in particular monopegylated or conjugated with a polyalkyl oxide moiety.
18. The activator of IFNλ receptor for the use, the use, or the method of any one of items 9-17, wherein the IFNλ is administered via intravenous, intraperitoneal, subcutaneous or intramuscular injection; via oral, topical or transmucosal administration; or via nasal or pulmonary inhalation.
19. The activator of IFNλ receptor for the use, the use, or the method of any one of items 9-17, wherein the IFNλ is administered via gene-therapy.
20. The activator of IFNλ receptor for the use, the use, or the method of any one of items 9-19, wherein the IFNλ is administered weekly.
21. The activator of IFNλ receptor for the use, the use, or the method of any one of items 9-19, wherein the IFNλ is administered every two weeks.
22. The activator of IFNλ receptor for the use, the use, or the method of any one of items 9-19, wherein the IFNλ is administered twice a week.
23. The activator of IFNλ receptor for the use, the use, or the method of any one of items 9-22, wherein the IFNλ is administered at a dose of 10 μg to 10 mg.
24. The activator of IFNλ receptor for the use, the use, or the method of item 23, wherein the IFNλ is administered at a dose of 100 μg to 9 mg.
25. The activator of IFNλ receptor for the use, the use, or the method of item 24, wherein the IFNλ is administered at a dose of 500 μg to 8 mg.
26. The activator of IFNλ receptor for the use, the use, or the method of item 25, wherein the IFNλ is administered at a dose of 1 mg to 7 mg.
27. The activator of IFNλ receptor for the use, the use, or the method of item 26, wherein the IFNλ is administered at a dose of 2 mg to 6 mg.
28. The activator of IFNλ receptor for the use, the use, or the method of item 27, wherein the IFNλ is administered at a dose of 5 mg.
29. The activator of IFNλ receptor for the use, the use, or the method of any one of items 9-22, wherein the IFNλ is administered at a dose of 0.1-150 μg/kg body weight.
30. The activator of IFNλ receptor for the use, the use, or the method of item 29, wherein the IFNλ is administered at a dose of 0.5-100 μg/kg body weight.
31. The activator of IFNλ receptor for the use, the use, or the method of item 30, wherein the IFNλ is administered at a dose of 1-90 μg/kg body weight.
32. The activator of IFNλ receptor for the use, the use, or the method of item 31, wherein the IFNλ is administered at a dose of 10-80 μg/kg body weight.
33. The activator of IFNλ receptor for the use, the use, or the method of item 32, wherein the IFNλ is administered at a dose of 20-70 μg/kg body weight.
34. The activator of IFNλ receptor for the use, the use, or the method of item 33, wherein the IFNλ is administered at a dose of 60 μg/kg body weight.
35. A method of determining susceptibility of a subject suffering from a coagulation disorder to treatment with an activator of IFNλ receptor, wherein the method comprises administering the activator of IFNλ receptor to the subject and determining the effect on the coagulation disorder.
36. An activator of IFNλ receptor for use in determining susceptibility of a subject suffering from a coagulation disorder to treatment with the activator of IFNλ receptor, wherein the activator of IFNλ receptor is administered to the subject and the effect on the coagulation disorder is determined.

37. A pharmaceutical composition comprising an activator of IFNλ receptor and a pharmaceutically acceptable excipient for use in the treatment of a coagulation disorder.

LITERATURE

Abushahba W, Balan M, Castaneda I, Yuan Y, Reuhl K, Raveche E, de la Torre A, Lasfar A, Kotenko S V (2010) Antitumor activity of type I and type III interferons in BNL hepatoma model. Cancer immunology, immunotherapy: CII 59: 1059-1071

Ank N, West H, Bartholdy C, Eriksson K, Thomsen A R, Paludan S R (2006) Lambda interferon (IFN-lambda), a type III IFN, is induced by viruses and IFNs and displays potent antiviral activity against select virus infections in vivo. J Virol 80: 4501-4509

Aspinall R J, Pockros P J (2004) The management of side-effects during therapy for hepatitis C. Alimentary pharmacology & therapeutics 20: 917-929

Bullens D M, Decraene A, Dilissen E, Meyts I, De Boeck K, Dupont L J, Ceuppens J L (2008) Type III IFN-lambda mRNA expression in sputum of adult and school-aged asthmatics. Clinical and experimental allergy: journal of the British Society for Allergy and Clinical Immunology 38: 1459-1467

Contoli M, Message S D, Laza-Stanca V, Edwards M R, Wark P A, Bartlett N W, Kebadze T, Mallia P, Stanciu L A, Parker H L et al (2006) Role of deficient type III interferon-lambda production in asthma exacerbations. Nature medicine 12: 1023-1026

Dai J, Megjugorac N J, Gallagher G E, Yu R Y, Gallagher G (2009) IFN-lambda1 (IL-29) inhibits GATA3 expression and suppresses Th2 responses in human naive and memory T cells. Blood 113: 5829-5838

Durbin R K, Kotenko S V, Durbin J E (2013) Interferon induction and function at the mucosal surface. Immunol Rev 255: 25-39

Gad H H, Dellgren C, Hamming O J, Vends S, Paludan S R, Hartmann R (2009) Interferon-lambda is functionally an interferon but structurally related to the interleukin-10 family. The Journal of biological chemistry 284: 20869-20875

Galani I E, Koltsida O, Andreakos E. Type III interferons (IFNs) (2015) Emerging Master Regulators of Immunity. Adv Exp Med Biol. 850:1-15

Galani I E, Triantafyllia V, Eleminiadou E E, Koltsida O, Stavropoulos A, Manioudaki M, Thanos D, Doyle S E, Kotenko S V, Thanopoulou K, Andreakos E (2017). Interferon-λ Mediates Non-redundant Front-Line Antiviral Protection against Influenza Virus Infection without Compromising Host Fitness. Immunity. 16; 46(5):875-890

Hernandez P P, Mahlakoiv T, Yang I, Schwierzeck V, Nguyen N, Guendel F, Gronke K, Ryffel B, Holscher C, Dumoutier L et al (2015) Interferon-lambda and interleukin 22 act synergistically for the induction of interferon-stimulated genes and control of rotavirus infection. Nat Immunol 16: 698-707

Jordan W J, Eskdale J, Boniotto M, Rodia M, Kellner D, Gallagher G (2007a) Modulation of the human cytokine response by interferon lambda-1 (IFN-lambda1/IL-29). Genes Immun 8: 13-20

Jordan W J, Eskdale J, Srinivas S, Pekarek V, Kelner D, Rodia M, Gallagher G (2007b) Human interferon lambda-1 (IFN-lambda1/IL-29) modulates the Th1/Th2 response. Genes Immun 8: 254-261

Koltsida O, Hausding M, Stavropoulos A, Koch S, Tzelepis G, Ubel C, Kotenko S V, Sideras P, Lehr H A, Tepe M et al (2011) IL-28A (IFN-lambda2) modulates lung D C function to promote Th1 immune skewing and suppress allergic airway disease. EMBO Mol Med 3: 348-361

Kotenko S V (2011) IFN-lambdas. Curr Opin Immunol 23: 583-590

Kotenko S V, Gallagher G, Baurin V V, Lewis-Antes A, Shen M, Shah N K, Langer J A, Sheikh F, Dickensheets H, Donnelly R P (2003) IFN-lambdas mediate antiviral protection through a distinct class II cytokine receptor complex. Nat Immunol 4: 69-77

Lasfar A, Lewis-Antes A, Smirnov S V, Anantha S, Abushahba W, Tian B, Reuhl K, Dickensheets H, Sheikh F, Donnelly R P et al (2006) Characterization of the mouse IFN-lambda ligand-receptor system: IFN-lambdas exhibit antitumor activity against B16 melanoma. Cancer research 66: 4468-4477

Lazear H M, Nice T J, Diamond M S (2015) Interferon-lambda: Immune Functions at Barrier Surfaces and Beyond. Immunity 43: 15-28

Li W, Lewis-Antes A, Huang J, Balan M, Kotenko S V (2008) Regulation of apoptosis by type III interferons. Cell proliferation 41: 960-979

Lin J D, Feng N, Sen A, Balan M, Tseng H C, McElrath C, Smirnov S V, Peng J, Yasukawa L L, Durbin R K, Durbin J E, Greenberg H B, Kotenko S V (2016). Distinct Roles of Type I and Type III Interferons in Intestinal Immunity to Homologous and Heterologous Rotavirus Infections. PLoS Pathog. 12(4):e1005600.

Maher S G, Sheikh F, Scarzello A J, Romero-Weaver A L, Baker D P, Donnelly R P, Gamero A M (2008) IFNalpha and IFNlambda differ in their antiproliferative effects and duration of JAK/STAT signaling activity. Cancer biology & therapy 7: 1109-1115

Mahlakoiv T, Hernandez P, Gronke K, Diefenbach A, Staeheli P (2015) Leukocyte-derived IFN-alpha/beta and epithelial IFN-lambda constitute a compartmentalized mucosal defense system that restricts enteric virus infections. PLoS Pathog 11: e1004782

Megjugorac N J, Gallagher G E, Gallagher G (2009) Modulation of human plasmacytoid D C function by IFN-lambda1 (IL-29). Journal of leukocyte biology 86: 1359-1363

Mendoza J L, Schneider W M, Hoffmann H H, Vercauteren K, Jude K M, Xiong A, Moraga I, Horton T M, Glenn J S, de Jong Y P, Rice C M, Garcia K C (2017) The IFN-λ-IFN-λR1-IL-10Rβ Complex Reveals Structural Features Underlying Type III IFN Functional Plasticity. Immunity 46(3):379-392

Mennechet F J, Uze G (2006) Interferon-lambda-treated dendritic cells specifically induce proliferation of FOXP3-expressing suppressor T cells. Blood 107: 4417-4423

Misumi I, Whitmire J K (2014) IFN-λ exerts opposing effects on T cell responses depending on the chronicity of the virus infection. J Immunol 192:3596-606

Mordstein M, Michiels T, Staeheli P (2010) What have we learned from the IL28 receptor knockout mouse? J Interferon Cytokine Res 30: 579-584

Morrow M P, Yan J, Pankhong P, Shedlock D J, Lewis M G, Talbott K, Toporovski R, Khan A S, Sardesai N Y, Weiner D B (2010) IL-28B/IFN-lambda 3 drives granzyme B loading and significantly increases CTL killing activity in macaques. Molecular therapy: the journal of the American Society of Gene Therapy 18: 1714-1723

Numasaki M, Tagawa M, Iwata F, Suzuki T, Nakamura A, Okada M, Iwakura Y, Aiba S, Yamaya M (2007) IL-28 elicits antitumor responses against murine fibrosarcoma. J Immunol 178: 5086-5098

Odendall C, Dixit E, Stavru F, Bierne H, Franz K M, Durbin A F, Boulant S, Gehrke L, Cossart P, Kagan J C (2014) Diverse intracellular pathogens activate type III interferon expression from peroxisomes. Nature immunology 15: 717-726

Onoguchi K, Yoneyama M, Takemura A, Akira S, Taniguchi T, Namiki H, Fujita T (2007) Viral infections activate types I and III interferon genes through a common mechanism. The Journal of biological chemistry 282: 7576-7581

Osterlund P I, Pietila T E, Veckman V, Kotenko S V, Julkunen 1 (2007) IFN regulatory factor family members differentially regulate the expression of type III IFN (IFN-lambda) genes. J Immunol 179: 3434-3442

Pekarek V, Srinivas S, Eskdale J, Gallagher G (2007) Interferon lambda-1 (IFN-lambda1/IL-29) induces ELR (−) CXC chemokine mRNA in human peripheral blood mononuclear cells, in an IFN-gamma-independent manner. Genes and immunity 8: 177-180

Pott J, Mahlakoiv T, Mordstein M, Duerr C U, Michiels T, Stockinger S, Staeheli P, Hornef M W (2011) IFN-lambda determines the intestinal epithelial antiviral host defense. Proc Natl Acad Sci USA 108: 7944-7949

Prokunina-Olsson L, Muchmore B, Tang W, Pfeiffer R M, Park H, Dickensheets H, Hergott D, Porter-Gill P, Mumy A, Kohaar I et al (2013) A variant upstream of IFNL3 (IL28B) creating a new interferon gene IFNL4 is associated with impaired clearance of hepatitis C virus. Nat Genet 45: 164-171

Ramos E L (2010) Preclinical and clinical development of pegylated interferon-lambda 1 in chronic hepatitis C. Journal of interferon & cytokine research: the official journal of the International Society for Interferon and Cytokine Research 30: 591-595

Robek M D, Boyd B S, Chisari F V (2005) Lambda interferon inhibits hepatitis B and C virus replication. Journal of virology 79: 3851-3854

Sato A, Ohtsuki M, Hata M, Kobayashi E, Murakami T (2006) Antitumor activity of IFN-lambda in murine tumor models. J Immunol 176: 7686-7694

Sheppard P, Kindsvogel W, Xu W, Henderson K, Schlutsmeyer S, Whitmore T E, Kuestner R, Garrigues U, Birks C, Roraback J et al (2003) IL-28, IL-29 and their class II cytokine receptor IL-28R. Nat Immunol 4: 63-68

Sommereyns C, Paul S, Staeheli P, Michiels T (2008) IFN-lambda (IFN-lambda) is expressed in a tissue-dependent fashion and primarily acts on epithelial cells in vivo. PLoS pathogens 4: e1000017

Thomson S J, Goh F G, Banks H, Krausgruber T, Kotenko S V, Foxwell B M, Udalova I A (2009) The role of transposable elements in the regulation of IFN-lambda1 gene expression. Proc Natl Acad Sci USA 106: 11564-11569

Witte K, Gruetz G, Volk H D, Looman A C, Asadullah K, Sterry W, Sabat R, Wolk K (2009) Despite IFN-lambda receptor expression, blood immune cells, but not keratinocytes or melanocytes, have an impaired response to type III interferons: implications for therapeutic applications of these cytokines. Genes and immunity 10: 702-714

Yin Z, Dai J, Deng J, Sheikh F, Natalia M, Shih T, Lewis-Antes A, Amrute S B, Garrigues U, Doyle S et al (2012) Type III IFNs are produced by and stimulate human plasmacytoid dendritic cells. J Immunol 189: 2735-2745

Zitzmann K, Brand S, Baehs S, Goke B, Meinecke J, Spottl G, Meyer H, Auernhammer C J (2006) Novel interferon-lambdas induce antiproliferative effects in neuroendocrine tumor cells. Biochemical and biophysical research communications 344: 1334-1341

In view of the above, it will be apparent that the present invention inter alia comprises the following items:

1. An activator of IFNλ receptor for use in the prevention or treatment of an obesity-related disorder in a subject.
2. A method of preventing or treating an obesity-related disorder in a subject comprising administering a therapeutically effective amount of an activator of IFNλ receptor to the subject in need of such treatment or prevention.
3. The activator of IFNλ receptor for the use or the method of item 1 or item 2, wherein the obesity-related disorder is selected from the group consisting of obesity, hyperphagia, prediabetes, diabetes (including type 1 diabetes, type 2 diabetes, and gestational diabetes), insulin resistance, metabolic disease, metabolic syndrome, coronary heart disease, carotid artery disease, myocardial infarction, stroke, thrombosis, dyslipidemia, hyperlipidemia or hypercholesterolemia.
4. The activator of IFNλ receptor for the use or the method of item 3, wherein the obesity-related disorder is obesity.
5. The activator of IFNλ receptor for the use or the method of item 3, wherein the diabetes is type 1 diabetes or type 2 diabetes.
6. An activator of IFNλ receptor for use in the prevention or treatment of atherosclerosis in a subject.
7. A method of preventing or treating atherosclerosis in a subject comprising administering a therapeutically effective amount of an activator of IFNλ receptor to the subject in need of such treatment or prevention.
8. The activator of IFNλ receptor for the use or the method of item 6 or item 7, wherein said treatment or prevention is reduction or prevention of atheromatic plaque formation and rupture, respectively.
9. An activator of IFNλ receptor for use in the prevention or treatment of a coagulation disorder in a subject.
10. A method of preventing or treating a coagulation disorder in a subject comprising administering a therapeutically effective amount of an activator of IFNλ receptor to the subject in need of such treatment or prevention.
11. The activator of IFNλ receptor for the use or the method of item 9 or item 10, wherein the coagulation disorder is thrombosis.
12. An activator of IFNλ receptor for use in the therapeutic reduction of body weight in a subject.
13. A method for therapeutic reduction of body weight in a subject comprising administering an activator of IFNλ receptor to the subject.
14. An activator of IFNλ receptor for use in the therapeutic reduction of overweight in a subject.
15. A method for therapeutic reduction of overweight in a subject comprising administering an activator of IFNλ receptor to the subject.
16. Use of an activator of IFNλ receptor for the non-therapeutic reduction of body weight in a subject, optionally wherein the non-therapeutic reduction of body weight involves the suppression of appetite and/or the suppression of overeating.
17. A method for non-therapeutic reduction of body weight in a subject comprising administering an activator of IFNλ receptor to the subject, optionally wherein the non-therapeutic reduction of body weight involves the suppression of appetite and/or the suppression of overeating.
18. Use of an activator of IFNλ receptor for the non-therapeutic reduction of overweight in a subject, optionally wherein the non-therapeutic reduction of overweight involves the suppression of appetite and/or the suppression of overeating.
19. A method for non-therapeutic reduction of overweight in a subject comprising administering an activator of IFNλ receptor to the subject, optionally wherein the non-therapeutic reduction of overweight involves the suppression of appetite and/or the suppression of overeating.
20. The activator of IFNλ receptor for the use, the use, or the method of any one of items 1-19, wherein the subject is a mammalian subject.
21. The activator of IFNλ receptor for the use, the use, or the method of any one of items 1-20, wherein the subject is a human.
22. The activator of IFNλ receptor for the use, the use, or the method of any one of items 1-21, wherein the activator of IFNλ receptor is administered in combination with one or more further therapeutic agent(s).
23. The activator of IFNλ receptor for the use, the use, or the method of item 22, wherein the further therapeutic agent(s) is/are selected from the group consisting of insulin, metformin (Glucophage), meglitinides (Prandin and Starlix), sulfonylureas (glyburide/DiaBeta, glipizide/Glucotrol and Glimepiride/Amaryl), canagliflozin (Invokana) and dapagliflozin (Farxiga), thiazolidinediones, such as pioglitazone (Actos), acarbose (Precose), pramlintide (Symlin), exenatide (Byetta), liraglutide (Victoza), long-acting exenatide (Bydureon), albiglutide (Tanzeum), dulaglutide (Trulicity), DPP-IV inhibitors (sitagliptin, saxagliptin, linagliptin), phentermine, diethylpropion, phendimetrazine, benzphetamine, oxyntomodulin, fluoxetine hydrochloride, qnexa (topiramate and phentermine), excalia (bupropion and zonisamide), contrave (bupropion and naltrexone), xenical (Orlistat), cetilistat, and GT 389-255, statins, cholesterol lowering drugs such as proprotein convertase subtilisin kexin type 9 (PCSK9) inhibitors, ACE inhibitors, aldosterone inhibitors, angiotensin II receptor blockers, beta-blockers, calcium channel blockers, antiplatelets such as aspirin, clopidogrel (Plavix) or dipyridamole (Persantine), anti-coagulants such as warfarin (Coumadin), heparin, direct factor Xa inhibitors, direct thrombin inhibitors, hydralazine, diuretics, corticosteroids, non-steroidal anti-inflammatory drugs, anti-TNF, anti-IL-1 and anti-IL-6.
24. The activator of IFNλ receptor for the use, the use, or the method of any one of items 1-23, wherein the activator of IFNλ receptor is a small molecule, an antibody or an antibody fragment, a peptide, a polynucleotide expressing IFNλ, IFNλ or an IFNλ derivative.
25. The activator of IFNλ receptor for the use, the use, or the method of item 24, wherein the activator of IFNλ receptor is IFNλ.
26. The activator of IFNλ receptor for the use, the use, or the method of item 25, wherein the IFNλ is human IFNλ.
27. The activator of IFNλ receptor for the use, the use, or the method of item 26, wherein the IFNλ is selected from the group consisting of IFNλ1, IFNλ2, IFNλ3 and IFNλ4.
28. The activator of IFNλ receptor for the use, the use, or the method of item 27, wherein the IFNλ is IFNλ1.
29. The activator of IFNλ receptor for the use, the use, or the method of item 27, wherein the IFNλ is IFNλ2.
30. The activator of IFNλ receptor for the use, the use, or the method of item 27, wherein the IFNλ is IFNλ3.
31. The activator of IFNλ receptor for the use, the use, or the method of item 27, wherein the IFNλ is IFNλ4.
32. The activator of IFNλ receptor for the use, the use, or the method of any one of items 25-31, wherein a mammal is treated with homologous IFNλ.
33. The activator of IFNλ receptor for the use, the use, or the method of any one of items 25-32, wherein the IFNλ is pegylated, in particular monopegylated or conjugated with a polyalkyl oxide moiety.
34. The activator of IFNλ receptor for the use, the use, or the method of any one of items 25-33, wherein the IFNλ is administered via intravenous, intraperitoneal, subcutaneous or intramuscular injection; via oral, topical or transmucosal administration; or via nasal or pulmonary inhalation.
35. The activator of IFNλ receptor for the use, the use, or the method of any one of items 25-33, wherein the IFNλ is administered via gene-therapy.
36. The activator of IFNλ receptor for the use, the use, or the method of any one of items 25-35, wherein the IFNλ is administered weekly.
37. The activator of IFNλ receptor for the use, the use, or the method of any one of items 25-35, wherein the IFNλ is administered every two weeks.
38. The activator of IFNλ receptor for the use, the use, or the method of any one of items 25-35, wherein the IFNλ is administered twice a week.
39. The activator of IFNλ receptor for the use, the use, or the method of any one of items 25-38, wherein the IFNλ is administered at a dose of 10 μg to 10 mg.
40. The activator of IFNλ receptor for the use, the use, or the method of item 39, wherein the IFNλ is administered at a dose of 100 μg to 9 mg.
41. The activator of IFNλ receptor for the use, the use, or the method of item 40, wherein the IFNλ is administered at a dose of 500 μg to 8 mg.
42. The activator of IFNλ receptor for the use, the use, or the method of item 41, wherein the IFNλ is administered at a dose of 1 mg to 7 mg.
43. The activator of IFNλ receptor for the use, the use, or the method of item 42, wherein the IFNλ is administered at a dose of 2 mg to 6 mg.
44. The activator of IFNλ receptor for the use, the use, or the method of item 43, wherein the IFNλ is administered at a dose of 5 mg.
45. The activator of IFNλ receptor for the use, the use, or the method of any one of items 25-38, wherein the IFNλ is administered at a dose of 0.1-150 μg/kg body weight.
46. The activator of IFNλ receptor for the use, the use, or the method of item 45, wherein the IFNλ is administered at a dose of 0.5-100 μg/kg body weight.
47. The activator of IFNλ receptor for the use, the use, or the method of item 46, wherein the IFNλ is administered at a dose of 1-90 μg/kg body weight.
48. The activator of IFNλ receptor for the use, the use, or the method of item 47, wherein the IFNλ is administered at a dose of 10-80 μg/kg body weight.
49. The activator of IFNλ receptor for the use, the use, or the method of item 48, wherein the IFNλ is administered at a dose of 20-70 μg/kg body weight.

50. The activator of IFNλ receptor for the use, the use, or the method of item 49, wherein the IFNλ is administered at a dose of 60 µg/kg body weight.
51. A method of determining susceptibility of a subject suffering from an obesity-related disorder, atherosclerosis or a coagulation disorder to treatment with an activator of IFNλ receptor, wherein the method comprises administering the activator of IFNλ receptor to the subject and determining the effect on the obesity-related disorder, atherosclerosis or the coagulation disorder, respectively.
52. An activator of IFNλ receptor for use in determining susceptibility of a subject suffering from an obesity-related disorder, atherosclerosis or a coagulation disorder to treatment with the activator of IFNλ receptor, wherein the activator of IFNλ receptor is administered to the subject and the effect on the obesity-related disorder, atherosclerosis or the coagulation disorder is determined, respectively.
53. A pharmaceutical composition comprising an activator of IFNλ receptor and a pharmaceutically acceptable excipient for use in the treatment of an obesity-related disorder.
54. A pharmaceutical composition comprising an activator of IFNλ receptor and a pharmaceutically acceptable excipient for use in the treatment of atherosclerosis.
55. A pharmaceutical composition comprising an activator of IFNλ receptor and a pharmaceutically acceptable excipient for use in the treatment of a coagulation disorder.

The invention claimed is:

1. A method of treating an obesity-related disorder, atherosclerosis or a coagulation disorder, the method comprising administering to a subject in need thereof an effective amount of an activator of a lambda interferon (IFNλ) receptor, wherein the activator of the IFNλ receptor is an IFNλ polypeptide or a polynucleotide encoding the IFNλ polypeptide, and wherein the IFNλ polypeptide is a type III IFN.

2. The method of claim 1, wherein the obesity-related disorder, atherosclerosis or the coagulation disorder is selected from the group consisting of obesity, hyperphagia, prediabetes, type 2 diabetes, gestational diabetes, insulin resistance, metabolic disease, metabolic syndrome, coronary heart disease, carotid artery disease, myocardial infarction, stroke, thrombosis, dyslipidemia, hyperlipidemia, hypercholesterolemia, atheromatic plaque formation, and atheromatic plaque rupture.

3. The method of claim 1, comprising the therapeutic reduction of body weight or overweight in the subject.

4. The method of claim 1, wherein the subject is a mammalian subject.

5. The method of claim 4, wherein the subject is a human subject.

6. The method of claim 1, wherein the activator of the IFNλ receptor is administered in combination with one or more further therapeutic agents.

7. The method of claim 6, wherein the one or more further therapeutic agents are selected from the group consisting of insulin, metformin, meglitinides, sulfonylureas, glyburide, glipizide, glimepiride, canagliflozin, dapagliflozin, thiazolidinediones, pioglitazone, acarbose, pramlintide, exenatide, liraglutide, long-acting exenatide, albiglutide, dulaglutide, DPP-IV inhibitors, sitagliptin, saxagliptin, linagliptin, phentermine, diethylpropion, phendimetrazine, benzphetamine, oxyntomodulin, fluoxetine hydrochloride, topiramate, phentermine, bupropion, zonisamide, bupropion, naltrexone, xenical, cetilistat, GT 389-255, statins, cholesterol lowering drugs, proprotein convertase subtilisin kexin type 9 (PCSK9) inhibitors, ACE inhibitors, aldosterone inhibitors, angiotensin II receptor blockers, beta-blockers, calcium channel blockers, antiplatelets, aspirin, clopidogrel, dipyridamole, anti-coagulants, warfarin, heparin, direct factor Xa inhibitors, direct thrombin inhibitors, hydralazine, diuretics, corticosteroids, and non-steroidal anti-inflammatory drugs.

8. The method of claim 1, wherein the IFNλ polypeptide is a human IFNλ.

9. The method of claim 8, wherein the IFNλ polypeptide is selected from the group consisting of IFNλ1, IFNλ2, IFNλ3 and IFNλ4.

10. The method of claim 1, wherein the IFNλ polypeptide is homologous to the subject.

11. The method of claim 1, wherein the IFNλ polypeptide is pegylated.

12. The method of claim 11, wherein the IFNλ polypeptide is a monopegylated IFNλ polypeptide or an IFNλ polypeptide conjugated with a polyalkyl oxide moiety.

13. The method of claim 1, wherein the activator of the IFNλ receptor is administered via intravenous, intraperitoneal, subcutaneous or intramuscular injection; via oral, topical or transmucosal administration; via nasal or pulmonary inhalation; or via gene-therapy.

14. The method of claim 1, wherein the activator of the IFNλ receptor is administered
   (i) weekly,
   (ii) every two weeks, or
   (iii) twice a week.

15. The method of claim 1, wherein the activator of the IFNλ receptor is administered at a dose selected from
   (i) 10 µg to 10 mg, 100 µg to 9 mg, 500 µg to 8 mg, 1 mg to 7 mg, 2 mg to 6 mg, and 5 mg; or
   (ii) 0.1-150 µg/kg body weight, 0.5-100 µg/kg body weight, 1-90 µg/kg body weight, 10-80 µg/kg body weight, 20-70 µg/kg body weight, and 60 µg/kg body weight.

16. The method of claim 1, wherein the activator of the IFNλ receptor is administered as a pharmaceutical composition comprising the activator of the IFNλ receptor and a pharmaceutically acceptable excipient.

17. The method of claim 1, wherein the activator of the IFNλ receptor is the IFNλ polypeptide.

18. The method of claim 1, wherein the IFNλ polypeptide comprises an amino acid sequence having at least 90% sequence identity to the amino acid sequence of SEQ ID NO: 1, SEQ ID NO: 2, SEQ ID NO: 3, SEQ ID NO: 4, or SEQ ID NO: 5.

19. The method of claim 18, wherein the IFNλ polypeptide comprises the amino acid sequence of SEQ ID NO: 1, SEQ ID NO: 2, SEQ ID NO: 3, SEQ ID NO: 4, or SEQ ID NO: 5.

20. A non-therapeutic method of reducing body weight or overweight in a subject, the method comprising administering a non-therapeutically effective amount of an activator of IFNλ receptor to the subject, wherein the activator of the IFNλ receptor is an IFNλ polypeptide or a polynucleotide encoding the IFNλ polypeptide, and wherein the IFNλ polypeptide is a type III IFN, and optionally wherein the non-therapeutic reduction of body weight or overweight involves suppression of appetite and/or the suppression of overeating.

21. A method for determining susceptibility of a subject to treatment with an activator of IFNλ receptor, wherein the subject is suffering from an obesity-related disorder, atherosclerosis or a coagulation disorder, and wherein the method comprises administering the activator of IFNλ receptor to the subject and determining the effect of administering activator of IFNλ receptor to the subject on the obesity-related disorder, atherosclerosis or the coagulation disorder, wherein the activator of the IFNλ receptor is an IFNλ polypeptide or a polynucleotide encoding the IFNλ polypeptide, and wherein the IFNλ polypeptide is a type III IFN.

* * * * *

```
SEQUENCE LISTING

<160> NUMBER OF SEQ ID NOS: 5

<210> SEQ ID NO 1
<211> LENGTH: 200
<212> TYPE: PRT
<213> ORGANISM: Homo sapiens

<400> SEQUENCE: 1

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
        195                 200

<210> SEQ ID NO 2
<211> LENGTH: 200
<212> TYPE: PRT
<213> ORGANISM: Homo sapiens

<400> SEQUENCE: 2

Met Lys Leu Asp Met Thr Gly Asp Cys Thr Pro Val Leu Val Leu Met
1               5                   10                  15
```

Ala Ala Val Leu Thr Val Thr Gly Ala Val Pro Val Ala Arg Leu His
            20                  25                  30

Gly Ala Leu Pro Asp Ala Arg Gly Cys His Ile Ala Gln Phe Lys Ser
        35                  40                  45

Leu Ser Pro Gln Glu Leu Gln Ala Phe Lys Arg Ala Lys Asp Ala Leu
    50                  55                  60

Glu Glu Ser Leu Leu Lys Asp Cys Arg Cys His Ser Arg Leu Phe
65                  70                  75                  80

Pro Arg Thr Trp Asp Leu Arg Gln Leu Gln Val Arg Glu Arg Pro Met
                85                  90                  95

Ala Leu Glu Ala Glu Leu Ala Leu Thr Leu Lys Val Leu Glu Ala Thr
            100                 105                 110

Ala Asp Thr Asp Pro Ala Leu Val Asp Val Leu Asp Gln Pro Leu His
        115                 120                 125

Thr Leu His His Ile Leu Ser Gln Phe Arg Ala Cys Ile Gln Pro Gln
130                 135                 140

Pro Thr Ala Gly Pro Arg Thr Arg Gly Arg Leu His His Trp Leu Tyr
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
            180                 185                 190

Val Ala Ser Gly Asp Leu Cys Val
        195                 200

<210> SEQ ID NO 3
<211> LENGTH: 200
<212> TYPE: PRT
<213> ORGANISM: Homo sapiens

<400> SEQUENCE: 3

Met Lys Leu Asp Met Thr Gly Asp Cys Met Pro Val Leu Val Leu Met
1               5                   10                  15

Ala Ala Val Leu Thr Val Thr Gly Ala Val Pro Val Ala Arg Leu Arg
            20                  25                  30

Gly Ala Leu Pro Asp Ala Arg Gly Cys His Ile Ala Gln Phe Lys Ser
        35                  40                  45

Leu Ser Pro Gln Glu Leu Gln Ala Phe Lys Arg Ala Lys Asp Ala Leu
    50                  55                  60

Glu Glu Ser Leu Leu Lys Asp Cys Lys Cys Arg Ser Arg Leu Phe
65                  70                  75                  80

Pro Arg Thr Trp Asp Leu Arg Gln Leu Gln Val Arg Glu Arg Pro Val
                85                  90                  95

Ala Leu Glu Ala Glu Leu Ala Leu Thr Leu Lys Val Leu Glu Ala Thr
            100                 105                 110

Ala Asp Thr Asp Pro Ala Leu Gly Asp Val Leu Asp Gln Pro Leu His
        115                 120                 125

Thr Leu His His Ile Leu Ser Gln Leu Arg Ala Cys Ile Gln Pro Gln
130                 135                 140

Pro Thr Ala Gly Pro Arg Thr Arg Gly Arg Leu His His Trp Leu His
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys

```
                    180                 185                 190

Val Ala Ser Gly Asp Leu Cys Val
            195                 200

<210> SEQ ID NO 4
<211> LENGTH: 196
<212> TYPE: PRT
<213> ORGANISM: Homo sapiens

<400> SEQUENCE: 4

Met Thr Gly Asp Cys Met Pro Val Leu Val Leu Met Ala Ala Val Leu
1               5                   10                  15

Thr Val Thr Gly Ala Val Pro Val Ala Arg Leu Arg Gly Ala Leu Pro
            20                  25                  30

Asp Ala Arg Gly Cys His Ile Ala Gln Phe Lys Ser Leu Ser Pro Gln
        35                  40                  45

Glu Leu Gln Ala Phe Lys Arg Ala Lys Asp Ala Leu Glu Glu Ser Leu
    50                  55                  60

Leu Leu Lys Asp Cys Lys Cys Arg Ser Arg Leu Phe Pro Arg Thr Trp
65                  70                  75                  80

Asp Leu Arg Gln Leu Gln Val Arg Glu Arg Pro Val Ala Leu Glu Ala
                85                  90                  95

Glu Leu Ala Leu Thr Leu Lys Val Leu Glu Ala Thr Ala Asp Thr Asp
            100                 105                 110

Pro Ala Leu Gly Asp Val Leu Asp Gln Pro Leu His Thr Leu His His
        115                 120                 125

Ile Leu Ser Gln Leu Arg Ala Cys Ile Gln Pro Gln Pro Thr Ala Gly
    130                 135                 140

Pro Arg Thr Arg Gly Arg Leu His His Trp Leu His Arg Leu Gln Glu
145                 150                 155                 160

Ala Pro Lys Lys Glu Ser Pro Gly Cys Leu Glu Ala Ser Val Thr Phe
                165                 170                 175

Asn Leu Phe Arg Leu Leu Thr Arg Asp Leu Asn Cys Val Ala Ser Gly
            180                 185                 190

Asp Leu Cys Val
        195

<210> SEQ ID NO 5
<211> LENGTH: 179
<212> TYPE: PRT
<213> ORGANISM: Homo sapiens

<400> SEQUENCE: 5

Met Arg Pro Ser Val Trp Ala Ala Val Ala Ala Gly Leu Trp Val Leu
1               5                   10                  15

Cys Thr Val Ile Ala Ala Ala Pro Arg Arg Cys Leu Leu Ser His Tyr
            20                  25                  30

Arg Ser Leu Glu Pro Arg Thr Leu Ala Ala Ala Lys Ala Leu Arg Asp
        35                  40                  45

Arg Tyr Glu Glu Glu Ala Leu Ser Trp Gly Gln Arg Asn Cys Ser Phe
    50                  55                  60

Arg Pro Arg Arg Asp Pro Pro Arg Ser Ser Cys Ala Arg Leu Arg
65                  70                  75                  80

His Val Ala Arg Gly Ile Ala Asp Ala Gln Ala Val Leu Ser Gly Leu
                85                  90                  95

His Arg Ser Glu Leu Leu Pro Gly Ala Gly Pro Ile Leu Glu Leu Leu
```

```
                100                 105                 110
Ala Ala Ala Gly Arg Asp Val Ala Ala Cys Leu Glu Leu Ala Arg Pro
        115                 120                 125

Gly Ser Ser Arg Lys Val Pro Gly Ala Gln Lys Arg Arg His Lys Pro
        130                 135                 140

Arg Arg Ala Asp Ser Pro Arg Cys Arg Lys Ala Ser Val Val Phe Asn
145                 150                 155                 160

Leu Leu Arg Leu Leu Thr Trp Glu Leu Arg Leu Ala Ala His Ser Gly
                165                 170                 175

Pro Cys Leu
```